US010157686B1

(12) United States Patent
Reicher et al.

(10) Patent No.: US 10,157,686 B1
(45) Date of Patent: Dec. 18, 2018

(54) AUTOMATED DOCUMENT FILING

(71) Applicant: DR Systems, Inc., San Diego, CA (US)

(72) Inventors: Murray A. Reicher, Rancho Santa Fe, CA (US); Carol G. Sloyer, La Jolla, CA (US); Cole A. Genovese, Encinitas, CA (US); Christopher S. Franklin, San Diego, CA (US)

(73) Assignee: D.R. Systems, Inc., San Diego, CA (US)

( * ) Notice: Subject to any disclaimer, the term of this patent is extended or adjusted under 35 U.S.C. 154(b) by 187 days.

(21) Appl. No.: 14/043,165

(22) Filed: Oct. 1, 2013

Related U.S. Application Data

(63) Continuation of application No. 11/944,027, filed on Nov. 21, 2007, now Pat. No. 8,554,576.

(60) Provisional application No. 60/867,071, filed on Nov. 22, 2006.

(51) Int. Cl.
*G06F 17/00* (2006.01)
*G16H 10/60* (2018.01)

(52) U.S. Cl.
CPC .................................. *G16H 10/60* (2018.01)

(58) Field of Classification Search
CPC ........ G06Q 10/10; G06Q 30/06; G06Q 40/04; G16H 10/60; G06F 17/243
USPC .......................................................... 705/3
See application file for complete search history.

(56) References Cited

U.S. PATENT DOCUMENTS

| 4,672,683 A | 6/1987 | Matsueda |
| 5,123,056 A | 6/1992 | Wilson |
| 5,179,651 A | 1/1993 | Taaffe et al. |
| 5,431,161 A | 7/1995 | Ryals et al. |
| 5,452,416 A | 9/1995 | Hilton et al. |
| 5,542,003 A | 7/1996 | Wofford |
| 5,734,915 A | 3/1998 | Roewer |
| 5,740,267 A | 4/1998 | Echerer et al. |
| 5,779,634 A | 7/1998 | Ema et al. |
| 5,852,646 A | 12/1998 | Klotz et al. |

(Continued)

FOREIGN PATENT DOCUMENTS

WO   WO 2007/131157   11/2007

OTHER PUBLICATIONS

US 7,801,341, 09/2010, Fram et al. (withdrawn)

(Continued)

*Primary Examiner* — Hiep V Nguyen
(74) *Attorney, Agent, or Firm* — Michael Best & Friedrich LLP

(57) ABSTRACT

A document management device provides a user interface that receives an indication from a user of one or more series associated with an electronic document, such as a scanned or electronically completed medical-related form. In other embodiments, the document management device comprises document detection intelligence that determines a type of document and/or series for an electronic document. After determining a series associated with a document, one or more attributes that have previously been associated with the determined series are associated with the electronic document. The attributes associated with the electronic document may then be used to control user's rights to the document, indicate a type of viewer associated with the document, indicate a storage location for the document, and/or indicate a type of the electronic document, for example.

14 Claims, 8 Drawing Sheets

(56) References Cited

U.S. PATENT DOCUMENTS

| | | |
|---|---|---|
| 5,926,568 A | 7/1999 | Chaney et al. |
| 5,954,650 A | 9/1999 | Saito et al. |
| 5,976,088 A | 11/1999 | Urbano et al. |
| 5,986,662 A | 11/1999 | Argiro et al. |
| 5,987,345 A | 11/1999 | Engelmann et al. |
| 5,995,644 A | 11/1999 | Lai et al. |
| 6,066,328 A | 5/2000 | Ribier et al. |
| 6,115,486 A | 9/2000 | Cantoni |
| 6,128,002 A | 10/2000 | Leiper |
| 6,151,581 A | 11/2000 | Kraftson et al. |
| 6,175,643 B1 | 1/2001 | Lai et al. |
| 6,177,937 B1 | 1/2001 | Stockham et al. |
| 6,185,320 B1 | 2/2001 | Bick et al. |
| 6,243,095 B1 | 6/2001 | Shile et al. |
| 6,269,379 B1 | 7/2001 | Hiyama et al. |
| 6,304,667 B1 | 10/2001 | Reitano |
| 6,347,329 B1 | 2/2002 | Evans |
| 6,351,547 B1 | 2/2002 | Johnson et al. |
| 6,383,135 B1 | 5/2002 | Chikovani et al. |
| 6,388,687 B1 | 5/2002 | Brackett et al. |
| 6,424,996 B1 | 7/2002 | Killcommons et al. |
| 6,438,533 B1 | 8/2002 | Spackman et al. |
| 6,463,169 B1 | 10/2002 | Ino et al. |
| 6,532,299 B1 | 3/2003 | Sachdeva et al. |
| 6,532,311 B1 | 3/2003 | Pritt |
| 6,544,531 B1 | 4/2003 | Cole et al. |
| 6,556,695 B1 | 4/2003 | Packer et al. |
| 6,556,724 B1 | 4/2003 | Chang et al. |
| 6,563,950 B1 | 5/2003 | Wiskott et al. |
| 6,574,629 B1 | 6/2003 | Cooke et al. |
| 6,577,753 B2 | 6/2003 | Ogawa |
| 6,603,494 B1 | 8/2003 | Banks et al. |
| 6,606,171 B1 | 8/2003 | Renk et al. |
| 6,618,060 B1 | 9/2003 | Brackett |
| 6,630,937 B2 | 10/2003 | Kallergi et al. |
| 6,678,764 B2 | 1/2004 | Parvelescu et al. |
| 6,697,067 B1 | 2/2004 | Callahan et al. |
| 6,697,506 B1 | 2/2004 | Oian et al. |
| 6,734,880 B2 | 5/2004 | Chang et al. |
| 6,760,755 B1 | 7/2004 | Brackett |
| 6,775,402 B2 | 8/2004 | Bacus et al. |
| 6,778,689 B1 | 8/2004 | Aksit et al. |
| 6,820,093 B2 | 11/2004 | de la Huerga |
| 6,820,100 B2 | 11/2004 | Funahashi |
| 6,829,377 B2 | 12/2004 | Milioto |
| 6,864,794 B2 | 3/2005 | Betz |
| 6,886,133 B2 | 4/2005 | Bailey et al. |
| 6,891,920 B1 | 5/2005 | Minyard et al. |
| 6,894,707 B2 | 5/2005 | Nemoto |
| 6,909,436 B1 | 6/2005 | Pianykh et al. |
| 6,909,795 B2 | 6/2005 | Tecotzky et al. |
| 6,917,696 B2 | 7/2005 | Soenksen |
| 6,988,075 B1 | 1/2006 | Hacker |
| 6,996,205 B2 | 2/2006 | Capolunghi et al. |
| 7,016,952 B2 | 3/2006 | Mullen et al. |
| 7,022,073 B2 | 4/2006 | Fan et al. |
| 7,027,633 B2 | 4/2006 | Foran et al. |
| 7,031,846 B2 | 4/2006 | Kaushikkar et al. |
| 7,043,474 B2 | 5/2006 | Mojsilovic |
| 7,050,620 B2 | 5/2006 | Heckman |
| 7,054,473 B1 | 5/2006 | Roehrig et al. |
| 7,058,901 B1 | 6/2006 | Hafey et al. |
| 7,092,572 B2 | 8/2006 | Huang et al. |
| 7,103,205 B2 | 9/2006 | Wang et al. |
| 7,106,479 B2 | 9/2006 | Roy et al. |
| 7,110,616 B2 | 9/2006 | Ditt et al. |
| 7,113,186 B2 | 9/2006 | Kim et al. |
| 7,123,684 B2 | 10/2006 | Jing et al. |
| 7,139,416 B2 | 11/2006 | Vuylsteke |
| 7,149,334 B2 | 12/2006 | Dehmeshki |
| 7,155,043 B2 | 12/2006 | Daw |
| 7,162,623 B2 | 1/2007 | Yngvesson |
| 7,170,532 B2 | 1/2007 | Sako |
| 7,174,054 B2 | 2/2007 | Manber et al. |
| 7,209,149 B2 | 4/2007 | Jogo |
| 7,212,661 B2 | 5/2007 | Samara et al. |
| 7,218,763 B2 | 5/2007 | Belykh et al. |
| 7,224,852 B2 | 5/2007 | Lipton et al. |
| 7,260,249 B2 | 8/2007 | Smith |
| 7,263,710 B1 | 8/2007 | Hummell et al. |
| 7,272,610 B2 | 9/2007 | Torres |
| 7,346,199 B2 | 3/2008 | Pfaff |
| 7,366,992 B2 | 4/2008 | Thomas, III |
| 7,412,111 B2 | 8/2008 | Battle et al. |
| 7,450,747 B2 | 11/2008 | Jabri et al. |
| 7,505,782 B2 | 3/2009 | Chu |
| 7,525,554 B2 | 4/2009 | Morita et al. |
| 7,526,114 B2 | 4/2009 | Seul et al. |
| 7,526,132 B2 | 4/2009 | Koenig |
| 7,545,965 B2 | 6/2009 | Suzuki et al. |
| 7,583,861 B2 | 9/2009 | Hanna et al. |
| 7,613,335 B2 | 11/2009 | McLennan et al. |
| 7,634,121 B2 | 12/2009 | Novatzky et al. |
| 7,636,413 B2 | 12/2009 | Toth |
| 7,639,879 B2 | 12/2009 | Goto et al. |
| 7,656,543 B2 | 2/2010 | Atkins |
| 7,660,488 B2 | 2/2010 | Reicher et al. |
| 7,668,352 B2 | 2/2010 | Tecotzky et al. |
| 7,683,909 B2 | 3/2010 | Takekoshi |
| 7,698,152 B2 | 4/2010 | Reid |
| 7,716,277 B2 | 5/2010 | Yamatake |
| 7,787,672 B2 | 8/2010 | Reicher et al. |
| 7,834,891 B2 | 11/2010 | Yarger et al. |
| 7,835,560 B2 | 11/2010 | Vining et al. |
| 7,885,440 B2 | 2/2011 | Fram et al. |
| 7,920,152 B2 | 4/2011 | Fram et al. |
| 7,953,614 B1 | 5/2011 | Reicher |
| 7,970,625 B2 | 6/2011 | Reicher et al. |
| 8,019,138 B2 | 9/2011 | Reicher et al. |
| 8,046,044 B2 | 10/2011 | Stazzone et al. |
| 8,050,938 B1 * | 11/2011 | Green et al. .................. 705/2 |
| 8,065,166 B2 | 11/2011 | Maresh et al. |
| 8,094,901 B1 | 1/2012 | Reicher et al. |
| 8,217,966 B2 | 7/2012 | Fram et al. |
| 8,244,014 B2 | 8/2012 | Murray et al. |
| 8,292,811 B2 | 10/2012 | Relkuntwar et al. |
| 8,379,051 B2 | 2/2013 | Brown |
| 8,380,533 B2 | 2/2013 | Reicher et al. |
| 8,391,643 B2 | 3/2013 | Melbourne et al. |
| 8,406,491 B2 | 3/2013 | Gee et al. |
| 8,457,990 B1 | 6/2013 | Reicher et al. |
| 8,554,576 B1 | 10/2013 | Reicher et al. |
| 8,560,050 B2 | 10/2013 | Martin et al. |
| 8,610,746 B2 | 12/2013 | Fram et al. |
| 8,626,527 B1 | 1/2014 | Murray et al. |
| 8,693,757 B2 | 4/2014 | Gundel |
| 8,712,120 B1 | 4/2014 | Reicher et al. |
| 8,731,259 B2 | 5/2014 | Reicher et al. |
| 8,751,268 B1 | 6/2014 | Reicher et al. |
| 8,879,807 B2 | 11/2014 | Fram et al. |
| 8,913,808 B2 | 12/2014 | Reicher et al. |
| 9,042,617 B1 | 5/2015 | Reicher et al. |
| 9,075,899 B1 | 7/2015 | Reicher |
| 9,092,551 B1 | 7/2015 | Reicher |
| 9,092,727 B1 | 7/2015 | Reicher |
| 9,386,084 B1 | 7/2016 | Reicher et al. |
| 9,471,210 B1 | 10/2016 | Fram et al. |
| 9,501,627 B2 | 11/2016 | Reicher et al. |
| 9,501,863 B1 | 11/2016 | Fram et al. |
| 9,542,082 B1 | 1/2017 | Reicher et al. |
| 9,672,477 B1 | 6/2017 | Reicher et al. |
| 9,727,938 B1 | 8/2017 | Reicher et al. |
| 9,754,074 B1 | 9/2017 | Reicher et al. |
| 9,836,202 B1 | 12/2017 | Reicher et al. |
| 2001/0016822 A1 | 8/2001 | Bessette |
| 2001/0042124 A1 | 11/2001 | Barron |
| 2002/0016718 A1 | 2/2002 | Rothschild et al. |
| 2002/0021828 A1 | 2/2002 | Papier et al. |
| 2002/0039084 A1 | 4/2002 | Yamaguchi |
| 2002/0044696 A1 | 4/2002 | Sirohey et al. |
| 2002/0070970 A1 | 6/2002 | Wood et al. |
| 2002/0073429 A1 | 6/2002 | Beane et al. |
| 2002/0090124 A1 | 7/2002 | Soubelet et al. |
| 2002/0091659 A1 | 7/2002 | Beaulieu et al. |

(56) References Cited

U.S. PATENT DOCUMENTS

| | | |
|---|---|---|
| 2002/0103673 A1 | 8/2002 | Atwood |
| 2002/0103827 A1 | 8/2002 | Sesek |
| 2002/0106119 A1 | 8/2002 | Foran et al. |
| 2002/0110285 A1 | 8/2002 | Wang et al. |
| 2002/0144697 A1 | 10/2002 | Betz |
| 2002/0145941 A1 | 10/2002 | Poland et al. |
| 2002/0180883 A1 | 12/2002 | Tomizawa et al. |
| 2002/0188637 A1 | 12/2002 | Bailey et al. |
| 2003/0005464 A1 | 1/2003 | Gropper et al. |
| 2003/0016850 A1 | 1/2003 | Kaufman et al. |
| 2003/0028402 A1 | 2/2003 | Ulrich et al. |
| 2003/0037054 A1 | 2/2003 | Dutta et al. |
| 2003/0053668 A1 | 3/2003 | Ditt et al. |
| 2003/0065613 A1 | 4/2003 | Smith |
| 2003/0071829 A1 | 4/2003 | Bodicker et al. |
| 2003/0101291 A1 | 5/2003 | Mussack et al. |
| 2003/0115083 A1 | 6/2003 | Masarie et al. |
| 2003/0120516 A1 | 6/2003 | Perednia |
| 2003/0130973 A1 | 7/2003 | Sumner, II et al. |
| 2003/0140141 A1 | 7/2003 | Mullen et al. |
| 2003/0160095 A1 * | 8/2003 | Segal .......................... 235/375 |
| 2003/0164860 A1 | 9/2003 | Shen et al. |
| 2003/0184778 A1 | 10/2003 | Chiba |
| 2003/0187689 A1 | 10/2003 | Barnes et al. |
| 2003/0190062 A1 | 10/2003 | Noro et al. |
| 2003/0195416 A1 | 10/2003 | Toth |
| 2003/0204420 A1 | 10/2003 | Wilkes et al. |
| 2003/0215122 A1 | 11/2003 | Tanaka |
| 2004/0008900 A1 | 1/2004 | Jabri et al. |
| 2004/0015703 A1 | 1/2004 | Madison et al. |
| 2004/0024303 A1 | 2/2004 | Banks et al. |
| 2004/0068170 A1 | 4/2004 | Wang et al. |
| 2004/0086163 A1 | 5/2004 | Moriyama et al. |
| 2004/0088192 A1 | 5/2004 | Schmidt et al. |
| 2004/0105030 A1 | 6/2004 | Yamane |
| 2004/0105574 A1 | 6/2004 | Pfaff |
| 2004/0114714 A1 | 6/2004 | Minyard et al. |
| 2004/0141661 A1 | 7/2004 | Hanna et al. |
| 2004/0143582 A1 | 7/2004 | Vu |
| 2004/0161139 A1 | 8/2004 | Samara et al. |
| 2004/0161164 A1 | 8/2004 | Dewaele |
| 2004/0165791 A1 | 8/2004 | Kaltanji |
| 2004/0172306 A1 | 9/2004 | Wohl et al. |
| 2004/0174429 A1 | 9/2004 | Chu |
| 2004/0190780 A1 | 9/2004 | Shiibashi et al. |
| 2004/0197015 A1 | 10/2004 | Fan et al. |
| 2004/0202387 A1 | 10/2004 | Yngvesson |
| 2004/0243435 A1 | 12/2004 | Williams |
| 2004/0252871 A1 | 12/2004 | Tecotzky et al. |
| 2004/0254816 A1 | 12/2004 | Myers |
| 2004/0255252 A1 | 12/2004 | Rodriguez et al. |
| 2005/0010531 A1 | 1/2005 | Kushalnagar et al. |
| 2005/0027569 A1 | 2/2005 | Gollogly et al. |
| 2005/0027570 A1 | 2/2005 | Maier et al. |
| 2005/0043970 A1 | 2/2005 | Hsieh |
| 2005/0063575 A1 | 3/2005 | Ma et al. |
| 2005/0065424 A1 | 3/2005 | Shah et al. |
| 2005/0074157 A1 | 4/2005 | Thomas, III |
| 2005/0075544 A1 | 4/2005 | Shapiro et al. |
| 2005/0088534 A1 | 4/2005 | Shen et al. |
| 2005/0107689 A1 | 5/2005 | Sasano |
| 2005/0108058 A1 | 5/2005 | Weidner et al. |
| 2005/0113681 A1 | 5/2005 | DeFreitas et al. |
| 2005/0114178 A1 | 5/2005 | Krishnamurthy et al. |
| 2005/0114179 A1 | 5/2005 | Brackett et al. |
| 2005/0114283 A1 | 5/2005 | Pearson et al. |
| 2005/0171818 A1 | 8/2005 | McLaughlin |
| 2005/0184988 A1 | 8/2005 | Yanof et al. |
| 2005/0197860 A1 | 9/2005 | Joffe et al. |
| 2005/0238218 A1 | 10/2005 | Nakamura |
| 2005/0244041 A1 | 11/2005 | Tecotzky et al. |
| 2005/0273009 A1 | 12/2005 | Deischinger et al. |
| 2006/0008181 A1 | 1/2006 | Takekoshi |
| 2006/0031097 A1 | 2/2006 | Lipscher et al. |
| 2006/0050152 A1 | 3/2006 | Rai et al. |
| 2006/0058603 A1 | 3/2006 | Dave et al. |
| 2006/0061570 A1 | 3/2006 | Cheryauka et al. |
| 2006/0093198 A1 | 5/2006 | Fram et al. |
| 2006/0093199 A1 | 5/2006 | Fram et al. |
| 2006/0093207 A1 | 5/2006 | Reicher et al. |
| 2006/0095423 A1 | 5/2006 | Reicher et al. |
| 2006/0095426 A1 | 5/2006 | Takachio et al. |
| 2006/0106642 A1 | 5/2006 | Reicher et al. |
| 2006/0111941 A1 | 5/2006 | Blom |
| 2006/0122482 A1 | 6/2006 | Mariotti et al. |
| 2006/0171574 A1 | 8/2006 | DelMonego et al. |
| 2006/0181548 A1 | 8/2006 | Hafey |
| 2006/0230072 A1 | 10/2006 | Partovi et al. |
| 2006/0239573 A1 | 10/2006 | Novatzky et al. |
| 2006/0241979 A1 | 10/2006 | Sato et al. |
| 2006/0277075 A1 | 12/2006 | Salwan |
| 2006/0282408 A1 | 12/2006 | Wisely et al. |
| 2007/0050701 A1 * | 3/2007 | El Emam et al. ............ 715/505 |
| 2007/0055550 A1 | 3/2007 | Courtney et al. |
| 2007/0064984 A1 | 3/2007 | Vassa et al. |
| 2007/0067124 A1 | 3/2007 | Kimpe et al. |
| 2007/0073556 A1 | 3/2007 | Lau et al. |
| 2007/0106535 A1 | 5/2007 | Matsunaga |
| 2007/0106633 A1 | 5/2007 | Reiner |
| 2007/0109402 A1 | 5/2007 | Niwa |
| 2007/0124541 A1 | 5/2007 | Lang et al. |
| 2007/0159962 A1 | 7/2007 | Mathavu et al. |
| 2007/0162308 A1 | 7/2007 | Peters |
| 2007/0174079 A1 | 7/2007 | Kraus |
| 2007/0192140 A1 | 8/2007 | Gropper |
| 2007/0239481 A1 | 10/2007 | DiSilvestro et al. |
| 2008/0016111 A1 | 1/2008 | Keen |
| 2008/0059245 A1 | 3/2008 | Sakaida et al. |
| 2008/0100612 A1 | 5/2008 | Dastmalchi et al. |
| 2008/0103828 A1 | 5/2008 | Squilla et al. |
| 2008/0118120 A1 | 5/2008 | Wegenkittl et al. |
| 2008/0125846 A1 | 5/2008 | Battle et al. |
| 2008/0126982 A1 | 5/2008 | Sadikali et al. |
| 2008/0136838 A1 | 6/2008 | Goede et al. |
| 2008/0275913 A1 | 11/2008 | van Arragon et al. |
| 2008/0279439 A1 | 11/2008 | Minyard et al. |
| 2009/0005668 A1 | 1/2009 | West et al. |
| 2009/0028410 A1 | 1/2009 | Shimazaki |
| 2009/0080719 A1 | 3/2009 | Watt |
| 2009/0091566 A1 | 4/2009 | Turney et al. |
| 2009/0123052 A1 | 5/2009 | Ruth et al. |
| 2009/0129643 A1 | 5/2009 | Natanzon et al. |
| 2009/0132586 A1 | 5/2009 | Napora et al. |
| 2009/0150481 A1 | 6/2009 | Garcia et al. |
| 2009/0182577 A1 | 7/2009 | Squilla et al. |
| 2009/0198514 A1 | 8/2009 | Rhodes |
| 2009/0213034 A1 | 8/2009 | Wu et al. |
| 2009/0248442 A1 | 10/2009 | Pacheco et al. |
| 2009/0268986 A1 | 10/2009 | Holstein et al. |
| 2010/0053353 A1 | 3/2010 | Hunter et al. |
| 2010/0138239 A1 | 6/2010 | Reicher et al. |
| 2010/0198608 A1 | 8/2010 | Kaboff et al. |
| 2010/0201714 A1 | 8/2010 | Reicher et al. |
| 2010/0211409 A1 | 8/2010 | Kotula et al. |
| 2010/0246981 A1 | 9/2010 | Hu et al. |
| 2010/0299157 A1 | 11/2010 | Fram et al. |
| 2011/0016430 A1 | 1/2011 | Fram |
| 2011/0019886 A1 | 1/2011 | Mizuno |
| 2011/0110572 A1 | 5/2011 | Guehring et al. |
| 2011/0267339 A1 | 11/2011 | Fram et al. |
| 2011/0316873 A1 | 12/2011 | Reicher |
| 2012/0070048 A1 | 3/2012 | Van Den Brink |
| 2012/0130729 A1 | 5/2012 | Raizada et al. |
| 2012/0136794 A1 | 5/2012 | Kushalnagar et al. |
| 2012/0163684 A1 | 6/2012 | Natanzon et al. |
| 2012/0194540 A1 | 8/2012 | Reicher |
| 2013/0076681 A1 | 3/2013 | Sirpal et al. |
| 2013/0083023 A1 | 4/2013 | Fram |
| 2013/0159019 A1 | 6/2013 | Reicher et al. |
| 2013/0169661 A1 | 7/2013 | Reicher et al. |
| 2015/0306124 A1 | 10/2015 | Manetta et al. |
| 2017/0206324 A1 | 7/2017 | Reicher et al. |
| 2017/0308647 A1 | 10/2017 | Reicher et al. |

(56) References Cited

U.S. PATENT DOCUMENTS

OTHER PUBLICATIONS

US 8,208,705, 06/2012, Reicher et al. (withdrawn)
Crowley, Rebecca et al., Development of Visual Diagnostic Expertise in Pathology: an Information-processing Study, Jan. 2003, Journal of the American medical Informatics Association, vol. 10, No. 1, pp. 39-51.
Non-Final Office Action dated Aug. 28, 2007 in U.S. Appl. No. 11/179,384.
Final Office Action dated Jun. 26, 2008 in U.S. Appl. No. 11/179,384.
Non-Final Office Action dated Dec. 29, 2008 in U.S. Appl. No. 11/179,384.
Final Office Action dated Jul. 24, 2009, in U.S. Appl. No. 11/179,384.
Notice of Allowance dated Nov. 3, 2009, in U.S. Appl. No. 11/179,384.
Non-Final Office Action dated Aug. 18, 2010 in U.S. Appl. No. 12/702,976.
Interview Summary dated Dec. 1, 2010, in U.S. Appl. No. 12/702,976.
Final Office Action dated Feb. 17, 2011 in U.S. Appl. No. 12/702,976.
Interview Summary dated May 31, 2011 in U.S. Appl. No. 12/702,976.
Notice of Allowance dated Jul. 20, 2011, in U.S. Appl. No. 12/702,976.
Office Action dated Dec. 1, 2011, in U.S. Appl. No. 13/228,349.
Notice of Allowance dated Feb. 6, 2012, in U.S. Appl. No. 13/228,349.
Notice of Allowance dated Jul. 20, 2012, in U.S. Appl. No. 13/228,349.
Office Action dated Dec. 11, 2013, in U.S. Appl. No. 13/477,853.
Non-Final Office Action dated Oct. 1, 2009, in U.S. Appl. No. 11/268,261.
Notice of Allowance dated Feb. 2, 2010, in U.S. Appl. No. 11/268,261.
Interview Summary dated May 14, 2010, in U.S. Appl. No. 11/268,261.
Notice of Allowance dated May 17, 2010, in U.S. Appl. No. 11/268,261.
Supplemental Notice of Allowance dated Aug. 6, 2010, in U.S. Appl. No. 11/268,261.
Notice of Allowance dated Oct. 8, 2010, in U.S. Appl. No. 11/268,261.
Notice of Allowance dated Dec. 3, 2010, in U.S. Appl. No. 11/268,261.
Notice of Allowance dated Jan. 6, 2011, in U.S. Appl. No. 11/268,261.
Office Action dated May 16, 2011, in U.S. Appl. No. 12/857,915.
Interview Summary dated Sep. 6, 2011, in U.S. Appl. No. 12/857,915.
Final Office Action dated Dec. 15, 2011, in U.S. Appl. No. 12/857,915.
Office Action dated Jun. 12, 2012, in U.S. Appl. No. 12/857,915.
Office Action dated Aug. 23, 2013, in U.S. Appl. No. 12/857,915.
Non-Final Office Action dated May 13, 2009, in U.S. Appl. No. 11/265,979.
Final Office Action dated Dec. 22, 2009 in U.S. Appl. No. 11/265,979.
Non-Final Office Action dated Jul. 8, 2010 in U.S. Appl. No. 11/265,979.
Interview Summary dated Mar. 4, 2010 in U.S. Appl. No. 11/265,979.
Interview Summary dated Nov. 16, 2010 in U.S. Appl. No. 11/265,979.
Final Office Action dated Dec. 23, 2010 in U.S. Appl. No. 11/265,979.
Interview Summary dated Mar. 17, 2011 in U.S. Appl. No. 11/265,979.
Notice of Allowance dated May 26, 2011 in U.S. Appl. No. 11/265,979.
Office Action dated Jun. 8, 2012 in U.S. Appl. No. 13/171,081.
Interview Summary dated Jul. 31, 2012 in U.S. Appl. No. 13/171,081.
Final Office Action dated Oct. 12, 2012 in U.S. Appl. No. 13/171,081.
Interview Summary dated Nov. 6, 2012 in U.S. Appl. No. 13/171,081.
Notice of Allowance, dated Sep. 4, 2013, in U.S. Appl. No. 13/171,081.
Non-Final Office Action dated Aug. 24, 2009 in U.S. Appl. No. 11/268,262.
Non-Final Office Action dated Apr. 16, 2010 in U.S. Appl. No. 11/268,262.
Interview Summary dated Nov. 24, 2009 in U.S. Appl. No. 11/268,262.
Interview Summary dated May 12, 2010 in U.S. Appl. No. 11/268,262.
Final Office Action dated Oct. 28, 2010 in U.S. Appl. No. 11/268,262.
Interview Summary dated Dec. 1, 2010 in U.S. Appl. No. 11/268,262.
Notice of Allowance dated Dec. 1, 2010 in U.S. Appl. No. 11/268,262.
Notice of Allowance dated Feb. 25, 2011 in U.S. Appl. No. 11/268,262.
Non-Final Office Action dated Jan. 11, 2012 in U.S. Appl. No. 13/079,597.
Notice of Allowance dated Apr. 25, 2012, in U.S. Appl. No. 13/079,597.
Non-Final Office Action dated Apr. 4, 2013 in U.S. Appl. No. 13/535,758.
Notice of Allowance, dated Aug. 23, 2013 in U.S. Appl. No. 13/535,758.
Non-Final Office Action dated Jul. 27, 2009 in U.S. Appl. No. 11/265,978.
Notice of Allowance dated Nov. 19, 2009 in U.S. Appl. No. 11/265,978.
Notice of Allowance dated Apr. 19, 2010 in U.S. Appl. No. 11/265,978.
Supplemental Notice of Allowance dated May 3, 2010 in U.S. Appl. No. 11/265,978.
Supplemental Notice of Allowance dated Aug. 3, 2010 in U.S. Appl. No. 11/265,978.
Non-Final Office Action dated May 5, 2011 in U.S. Appl. No. 12/870,645.
Non-Final Office Action dated May 31, 2013, in U.S. Appl. No. 13/345,606.
Interview Summary dated Aug. 15, 2013, in U.S. Appl. No. 13/345,606.
Notice of Allowance, dated Jan. 9, 2014 in U.S. Appl. No. 13/345,606.
Non-Final Office Action dated May 26, 2010 in U.S. Appl. No. 11/942,674.
Interview Summary dated Jul. 26, 2010 in U.S. Appl. No. 11/942,674.
Final Office Action dated Nov. 26, 2010 in U.S. Appl. No. 11/942,674.
Interview Summary dated Mar. 2, 2011 in U.S. Appl. No. 11/942,674.
Notice of Allowance, dated Apr. 1, 2011 in U.S. Appl. No. 11/942,674.
Non Final Office Action dated Nov. 10, 2011 in U.S. Appl. No. 13/118,085.
Interview Summary, dated Feb. 17, 2012, in U.S. Appl. No. 13/118,085.
Final Office Action, dated Apr. 13, 2012, in U.S. Appl. No. 13/118,085.
Notice of Allowance, dated Feb. 6, 2013, in U.S. Appl. No. 13/118,085.
Non Final Office Action dated Aug. 23, 2013 in U.S. Appl. No. 13/907,128.
Final Office Action dated Oct. 9, 2013 in U.S. Appl. No. 13/907,128.
Interview Summary dated Nov. 22, 2013 in U.S. Appl. No. 13/907,128.
Non Final Office Action dated Sep. 16, 2010 in U.S. Appl. No. 11/942,687.
Interview Summary dated Dec. 3, 2010 in U.S. Appl. No. 11/942,687.
Final Office Action, dated Apr. 5, 2011 in U.S. Appl. No. 11/942,687.
Final Office Action dated Dec. 23, 2010 in U.S. Appl. No. 11/944,027.
Interview Summary dated Mar. 31, 2011 in U.S. Appl. No. 11/944,027.
Office Action dated Apr. 19, 2012 in U.S. Appl. No. 11/944,027.
Interview Summary dated Jun. 28, 2012 in U.S. Appl. No. 11/944,027.
Final Office Action dated Oct. 22, 2012 in U.S. Appl. No. 11/944,027.
Notice of Allowance dated Jun. 5, 2013 in U.S. Appl. No. 11/944,027.
Non-Final Office Action dated Sep. 29, 2010 in U.S. Appl. No. 11/944,000.
Final Office Action dated Apr. 20, 2011 in U.S. Appl. No. 11/944,000.
Interview Summary dated Jun. 7, 2011 in U.S. Appl. No. 11/944,000.
Appeal Brief dated Mar. 4, 2013 in U.S. Appl. No. 11/944,000.
Examiner's Answer dated Jun. 26, 2013 in U.S. Appl. No. 11/944,000.
Office Action dated Feb. 3, 2012 in U.S. Appl. No. 12/622,404.
Interview Summary dated May 8, 2012 in U.S. Appl. No. 12/622,404.
Final Office Action dated Aug. 6, 2012 in U.S. Appl. No. 12/622,404.
Notice of Allowance dated Oct. 15, 2012 in U.S. Appl. No. 12/622,404.
Office Action dated Mar. 4, 2013 in U.S. Appl. No. 12/891,543.
Interview Summary dated Apr. 5, 2013 in U.S. Appl. No. 12/891,543.
Mendelson, et al., "Informatics in Radiology—Image Exchange: IHE and the Evolution of Image Sharing," RadioGraphics, Nov.-Dec. 2008, vol. 28, No. 7.
U.S. Appl. No. 14/792,201, filed Jul. 6, 2015, Reicher.
Interview Summary dated May 1, 2015 in U.S. Appl. No. 14/095,123.
Final Office Action, dated Jun. 17, 2015 in U.S. Appl. No. 14/298,806.
Interview Summary dated Jun. 11, 2015 in U.S. Appl. No. 13/768,765.

(56) References Cited

OTHER PUBLICATIONS

Corrected Notice of Allowance, dated Apr. 10, 2015 in U.S. Appl. No. 13/572,547.
Corrected Notice of Allowance, dated May 21, 2015 in U.S. Appl. No. 13/572,547.
Interview Summary dated Apr. 23, 2015 in U.S. Appl. No. 13/572,552.
Notice of Allowance, dated May 8, 2015 in U.S. Appl. No. 13/572,552.
U.S. Appl. No. 12/437,522, filed May 7, 2009, Fram.
U.S. Appl. No. 13/572,397, filed Aug. 10, 2012, Reicher.
U.S. Appl. No. 13/572,547, filed Aug. 10, 2012, Reicher.
U.S. Appl. No. 13/572,552, filed Aug. 10, 2012, Reicher.
U.S. Appl. No. 14/687,853, filed Apr. 15, 2015, Reicher.
Interview Summary dated Mar. 14, 2014, in U.S. Appl. No. 13/477,853.
Final Office Action dated Jun. 13, 2014, in U.S. Appl. No. 13/477,853.
Notice of Allowance dated Aug. 15, 2014, in U.S. Appl. No. 13/477,853.
Interview Summary dated Jan. 25, 2010, in U.S. Appl. No. 11/268,261.
Issue Notice dated Sep. 1, 2010, in U.S. Appl. No. 11/268,261.
Interview Summary dated Feb. 4, 2014, in U.S. Appl. No. 12/857,915.
Notice of Allowance dated Jul. 3, 2014, in U.S. Appl. No. 12/857,915.
"Corrected" Notice of Allowance dated Aug. 15, 2014, in U.S. Appl. No. 12/857,915.
Office Action dated Mar. 3, 2015 in U.S. Appl. No. 14/095,123.
Notice of Allowance dated Jan. 31, 2014 in U.S. Appl. No. 13/907,128.
Office Action, dated Dec. 29, 2014 in U.S. Appl. No. 14/298,806.
Interview Summary, dated Mar. 2, 2015 in U.S. Appl. No. 14/298,806.
Interview Summary, dated Jun. 17, 2014 in U.S. Appl. No. 11/942,687.
Office Action, dated Jul. 18, 2014 in U.S. Appl. No. 11/942,687.
Interview Summary, dated Mar. 4, 2015 in U.S. Appl. No. 11/942,687.
Non-Final Office Action dated Apr. 14, 2010 in U.S. Appl. No. 11/944,027.
Interview Summary dated May 13, 2010 in U.S. Appl. No. 11/944,027.
Office Action dated Mar. 17, 2015 in U.S. Appl. No. 13/768,765.
Notice of Allowance dated Nov. 14, 2013 in U.S. Appl. No. 12/891,543.
Office Action dated Sep. 11, 2014 in U.S. Appl. No. 14/179,328.
Notice of Allowance dated Jan. 14, 2015 in U.S. Appl. No. 14/179,328.
Office Action dated Jun. 27, 2014 in U.S. Appl. No. 13/572,397.
Final Office Action dated Jan. 13, 2015 in U.S. Appl. No. 13/572,397.
Notice of Allowance dated Mar. 19, 2015, 2015 in U.S. Appl. No. 13/572,397.
Office Action dated Aug. 6, 2014 in U.S. Appl. No. 13/572,547.
Notice of Allowance, dated Mar. 3, 2015 in U.S. Appl. No. 13/572,547.
Office Action dated Jul. 30, 2014 in U.S. Appl. No. 13/572,552.
Interview Summary dated Sep. 3, 2014 in U.S. Appl. No. 13/572,552.
Final Office Action dated Jan. 28, 2015 in U.S. Appl. No. 13/572,552.
AGFA HealthCare, color brochure "IMPAX 6: Digital Image and Information Management," © 2012 Agfa HealthCare N.V. Downloaded from http://www.agfahealthcare.com/global/en/he/library/libraryopen?ID=32882925. Accessed on Feb. 9, 2015.
AGFA HealthCare, IMPAX 6.5 Datasheet (US)2012. © 2012 Agfa HealthCare N.V. Downloaded from http://www.agfahealthcare.com/global/en/he/library/libraryopen?ID=37459801. Accessed on Feb. 9, 2015.
AMD Technologies, Inc., Catella PACS 5.0 Viewer User Manual (112 pgs), © 2010, AMD Technologies, Inc. (Doc. 340-3-503 Rev. 01). Downloaded from http://www.amdtechnologies.com/lit/cat5viewer.pdf. Accessed on Feb. 9, 2015.
Aspyra's Imaging Solutions, 3 pages color print out. Accessed at http://www.aspyra.com/imaging-solutions. Accessed on Feb. 9, 2015.
AVREO, interWorks—RIS/PACS package, 2 page color brochure, © 2014, Avreo, Inc. (Document MR-5032 Rev. 4). Downloaded from http://www.avreo.com/ProductBrochures/MR-5032Rev.%204interWORKS%20RISPACSPackage.pdf. Accessed on Feb. 9, 2015.
BRIT Systems, BRIT PACS View Viewer, 2 page color brochure, (BPB-BPV-0001). Downloaded from http://www.brit.com/pdfs/britpacsview.pdf. Accessed on Feb. 9, 2015.
Brit Systems, Roentgen Works—100% Browers-based VNA (Vendor Neutral Archive/PACS), © 2010 BRIT Systems, 1 page color sheet. Accessed at http://www.roentgenworks.com/PACS. Accessed on Feb. 9, 2015.
Brit Systems, Vision Multi-modality Viewer—with 3D, 2 page color brochure, (BPB-BVV-0001 REVC). Downloaded from http://www.brit.com/pdfs/BPB-BVV-0001-REVC_BRIT_Vision_Viewer.pdf. Accessed on Feb. 9, 2015.
CANDELiS, ImageGrid™: Image Management Appliance, 6 page color brochure. (AD-012 Rev. F Nov. 2012), © 2012 Candelis, Inc. Downloaded from http://www.candelis.com/images/pdf/Candelis_ImageGrid_Appliance_20111121.pdf. Accessed on Feb. 9, 2015.
Carestream, Cardiology PACS, 8 page color brochure. (CAT 866 6075 Jun. 2012). © Carestream Health, Inc., 2012. Downloaded from http://www.carestream.com/cardioPACS_brochure_M1-877.pdf. Accessed on Feb. 9, 2015.
Carestream, Vue PACS, 8 page color brochure. (CAT 300 1035 May 2014). © Carestream Health, Inc., 2014. Downloaded from http://www.carestream.com/csPACS_brochure_M1-876.pdf. Accessed on Feb. 9, 2015.
Cerner, Radiology—Streamline image management, 2 page color brochure, (fl03_332_10_v3). Downloaded from http://www.cerner.com/uploadedFiles/Clinical_Imaging.pdf. Accessed on Feb. 9, 2015.
CoActiv, EXAM-PACS, 2 page color brochure, © 2014 CoActiv, LLC. Downloaded from http://coactiv.com/wp-content/uploads/2013/08/EXAM-PACS-BROCHURE-final-web.pdf. Accessed on Feb. 9, 2015.
DR Systems, Dominator™ Guide for Reading Physicians, Release 8.2, 546 pages, (TCP-000260-A), © 1997-2009, DR Systems, Inc. Downloaded from https://resources.dominator.com/assets/004/6999.pdf. Document accessed Feb. 9, 2015.
DR Systems, DR Scheduler User Guide, Release 8.2, 410 pages, (TCP-000115-A), © 1997-2009, DR Systems, Inc. Downloaded from https://resources.dominator.com/assets/003/6850.pdf. Document accessed Feb. 9, 2015.
Erickson, et al.: "Effect of Automated Image Registration on Radiologist Interpretation," Journal of Digital Imaging, vol. 20, No. 2 Jun. 2007; pp. 105-113.
Erickson, et al.: "Image Registration Improves Confidence and Accuracy of Image Interpretation," Special Issue-Imaging Informatics, Cancer Informatics 2007:1 19-24.
Fujifilm Medical Systems, SYNAPSE® Product Data, Synapse Release Version 3.2.1, Foundation Technologies, 4 page color brochure, (XBUSSY084) Aug. 2008. Downloaded from http://www.fujifilmusa.com/shared/bin/foundation.pdf. Accessed on Feb. 9, 2015.
FUJIFILM Medical Systems, SYNAPSE® Product Data, Synapse Release Version 3.2.1, Server Modules and Interfaces, 4 page color brochure, (XBUSSY085) Aug. 2008. Downloaded from http://www.fujifilmusa.com/shared/bin/server-interface.pdf. Accessed on Feb. 9, 2015.
FUJIFILM Medical Systems, SYNAPSE® Product Data, Synapse Release Version 3.2.1, Workstation Software, 4 page color brochure, (XBUSSY082) Aug. 2008. Downloaded from http://www.fujifilmusa.com/shared/bin/workstation.pdf. Accessed on Feb. 9, 2015.
GE Healthcare, Centricity PACS, in 8 page printout. Accessed at http://www3.gehealthcare.com/en/products/categories/healthcare_it/medical_imaging_informatics_-_ris-pacs-cvis/centricity_pacs. Accessed on Feb. 9, 2015.
Handylife.com—Overview of Handy Patients Enterprise, in 2 page printout. Accessed from http://www.handylife.com/en/software/overview.html. Accessed on Feb. 18, 2015.
Handylife.com—Features of Handy Patients Enterprise, in 4 page printout. Accessed from http://www.handylife.com/en/software/features.html. Accessed on Feb. 18, 2015.
Handylife.com—Screenshots of Handy Patients Enterprise, in 2 page printout. Accessed from http://www.handylife.com/en/software/screenshots.html. Accessed on Feb. 18, 2015.
ICRco, I See The Future, in 12 pages, color brochure, (BR080809AUS), © 2009 iCRco.ClarityPACS. Downloaded from http://www.claritypacs.com/pdfs/ISeeFuture_26_Web.pdf. Accessed on Feb. 9, 2015.
Imageanalysis, dynamika, 2 page color brochure. Downloaded from http://www.imageanalysis.org.uk/what-we-do. Accessed on Feb. 9, 2015.

(56) References Cited

OTHER PUBLICATIONS

Imageanalysis, MRI Software, in 5 page printout. Accessed at http://www.imageanalysis.org.uk/mri-software. Accessed on Feb. 9, 2015.
IMSI, Integrated Modular Systems, Inc., Hosted / Cloud PACS in one page printout. Accessed at http://www.imsimed.com/#!products-services/ctnu. Accessed on Feb. 9, 2015.
Infinitt, PACS, RIS, Mammo PACS, Cardiology Suite and 3D/Advanced Visualization | Infinittna, 2 page printout. Accessed at http://www.infinittna.com/products/radiology/radiology-pacs. Accessed on Feb. 9, 2015.
Intelerad, IntelePACS, 2 page color brochure, © 2014 Intelerad Medical Systems Incoprorated. Downloaded http://www.intelerad.com/wp-content/uploads/sites/2/2014/08/IntelePACS-brochure.pdf. Accessed on Feb. 9, 2015.
Intelerad, InteleViewer, 2 page color brochure, © 2014 Intelerad Medical Systems Incoprorated. Downloaded from http://www.intelerad.com/wp-content/uploads/sites/2/2014/09/InteleViewer-brochure.pdf. Accessed on Feb. 9, 2015.
Intuitive Imaging Informatics, ImageQube, 1 page in color. Downloaded from http://www.intuitiveimaging.com/2013/pdf/ImageQube%20one-sheet.pdf. Accessed on Feb. 9, 2015.
Kuhl, Helen: Comparison Chart/PACS, Customers Are Happy, But Looking for More, (color) Imaging Techology News, itnonline.com, May 2012, pp. 24-27. Downloaded from http://www.merge.com/MergeHealthcare/media/company/In%20The%20News/merge-pacs-comparison.pdf. Accessed on Feb. 9, 2015.
LUMEDX CardioPACS 5.0 Web Viewer, Cardiopacs Module, 2 page color brochure, (506-10011 Rev A). Downloaded from http://cdn.medicexchange.com/images/whitepaper/cardiopacs_web_viewer.pdf?1295436926. Accessed on Feb. 9, 2015.
LUMEDX Cardiovascular Information System, CardioPACS, one page in color printout. Accessed at http://www.lumedx..com/pacs.aspx. Accessed on Feb. 9, 2015.
McKesson Enterprise Medical Imagining and PACS | McKesson, 1 page (color) printout. Accessed at http://www.mckesson.com/providers/health-systems/diagnostic-imaging/enterprise-medical-imaging. Accessed on Feb. 9, 2015.
Medweb Radiology Workflow Solutions, Radiology Workflow Solutions, Complete Workflow & Flexible Turnkey Solutions, Web RIS/PACS with Advanced Viewer, 3 page color brochure, © 2006-2014 Medweb. Downloaded from http://www.medweb.com/docs/rispacs_brochure_2014.pdf. Accessed on Feb. 9, 2015.
Merge Radiology Solutions, Merge PACS, A real-time picture archiving communication system, (PAX-21990 rev 2.0), 2 page color brochure. Downloaded from http://www.merge.com/MergeHealthcare/media/documents/brochures/Merge_PACS_web.pdf. Accessed on Feb. 9, 2015.
NOVARAD Enterprise Imaging Solutions, NOVAPACS, 2 page (color) printout. Accessed at http://ww1.novarad.net/novapacs. Accessed on Feb. 9, 2015.
PACSPLUS, PACSPLUS Server, 1 page (color) printout. Accessed at http://www.pacsplus.com/01_products/products_01.html. Accessed on Feb. 9, 2015.
PACSPLUS, PACSPLUS Workstation, 3 page (color) printout. Accessed at http://www.pacsplus.com/01_products/products_01.html. Accessed on Feb. 9, 2015.
Philips IntelliSpace PACS, in 2 color page printout. Accessed at https://www.healthcare.philips.com/main/products/healthcare_informatics/products/enterprise_imaging_informatics/isite_pacs. Accessed on Feb. 9, 2015.
Philips, IntelliSpace: Multi-modality tumor tracking application versus manual PACS methods, A time study for Response Evaluation Criteria in Solid Tumors (RECIST). 2012, Koninklijke Philips Electronics N.V., in four pages.
Radcliffe, et al., "Comparison of Stereo Disc Photographs and Alternation Flicker Using a Novel Matching Technology for Detecting Glaucoma Progression", Ophthalmic Surgery, Lasers & Imaging, Jun. 9, 2010.
RamSoft, RIS PACS Teleradiology, PowerServer PACS, Lite PACS, XU PACS Compare RamSoft PACS Products, 2 color page printout. Accessed at http://www.ramsoft.com/products/powerserver-pacs-overview. Accessed on Feb. 9, 2015.
Sage Intergy PACS | Product Summary. Enhancing Your Workflow by Delivering Web-based Diagnostic Images When and Where You Need Them, in 2 color pages. (IRV-SS-INTPACS-PSS-031309). © 2009 Sage Software Healcare, Inc. Downloaded from http://www.greenwayhealth.com/solutions/intergy/. Accessed on Feb. 9, 2015.
Schellingerhout, Dawid, MD, et al.: "Coregistration of Head CT Comparison Studies: Assessment of Clinical Utility," Acad Radiol 2003; 10:242-248.
ScImage, Cardiology PACS, in 8 color page printout. Accessed at http://www.scimage.com/solutions/clinical-solutions/cardiology. Accessed on Feb. 9 2015.
Sectra RIS PACS, in 2 color page printout. Accessed at https://www.sectra.com/medical/diagnostic_imaging/solutions/ris-pacs/. Accessed on Feb. 9, 2015.
Siemens syngo.plaza, Features and Benefits, in 2 color page printout. Accessed at http://www.healthcare.siemens.com/medical-imaging-it/imaging-it-radiology-image-management-pacs/syngoplaza/features. Accessed on Feb. 9, 2015.
Simms | RIS and PACS Medical Imaging Software, in 2 color page printout. http://www.mysimms.com/ris-pacs.php. Accessed on Feb. 9, 2015.
Stryker, Imaging—OfficePACS Power Digital Imaging, in one color page printout. Accessed from http://www.stryker.com/emea/Solutions/Imaging/OfficePACSPowerDigitalImaging/index.htm. Accessed on Feb. 9, 2015.
Stryker, OfficePACS Power—Digital Imaging, 8 page color brochure, (MPP-022 Rev 4 BC/MP 300 Jan. 2007). © 2007 Stryker. Downloaded from http://www.stryker.com/emea/Solutions/Imaging/OfficePACSPowerDigitalImaging/ssLINK/emea/1557/022268. Accessed on Feb. 9, 2015.
Syed, et al., "Detection of Progressive Glaucomatous Optic Neuropathy Using Automated Alternation Flicker With Stereophotography," Research Letter, Arch Ophthalmol., published online Dec. 13, 2010. 2010 American Medical Association.
Syed, et al.. "Automated alternation flicker for the detection of optic disc haemorrhages", ACTA Ophthalmologica 2011, accepted for publication on Nov. 26, 2010.
Tay, et al., "Assessing Signal Intensity Change on Well-registered Images: Comparing Subtraction, Color-encoded Subtraction, and Parallel Display Formats", Original Research:Computer Applications. Radiology, vol. 260: No. 2—Aug. 2011.
UltraRAD—ultra VISION, 1 page (color). Downloaded from http://www.ultraradcorp.com/pdf/UltraVISION.pdf. Accessed on Feb. 9, 2015.
VanderBeek, et al., "Comparing the detection and agreement of parapapillary atrophy progression using digital optic disk photographs and alternation flicker", Glaucoma, Graefes Arch Clin Exp Ophthalmol (2010) 248:1313-1317, Apr. 15, 2010.
VioStream for VitreaView, 2 color pages printout. Accessed at http://www.vitalimages.com/solutions/universal-viewing/viostream-for-vitreaview. Accessed on Feb. 9, 2015.
Visage Imaging Visage 7, 3 color page printout. Accessed at http://www.visageimaging.com/visage-7. Accessed on Feb. 9, 2015.
VIZTEK Radiology PACS Software Vixtek Opal-RAD, 4 color page printout. Accessed at http://viztek.net/products/opal-rad. Accessed on Feb. 9, 2015.
Voyager Imaging—Voyager PACS Radiologist Workstation, 2 page color brochure. Downloaded from http://www.intellirad.com.au/assets/Uploads/Voyager-PacsWorkstations.pdf?. Accessed on Feb. 9, 2015.
Voyager Imaging—Voyager PACS, 3 page color brochure. Downloaded from http://www.intellirad.com.au/index.php/assets/Uploads/Voyager-Pacs3.pdf. Accessed on Feb. 9, 2015.
Ivetic, D., and Dragan, D., Medical Image on the Go!, 2009, J Med Syst, vol. 35, pp. 499-516.
Tahmoush, D. and Samet, H., A New Database for Medical Images and Information, 2007, Medical Imaging 2007; PACS and Imaging Informatics, vol. 6516. pp. 1-9.

(56) References Cited

OTHER PUBLICATIONS

U.S. Appl. No. 14/540,830, filed Nov. 13, 2014 including its ongoing prosecution history, including without limitation Office Actions, Amendments, Remarks, and any other potentially relevant documents, Reicher et al.
U.S. Appl. No. 14/502,055, filed Sep. 30, 2014 including its ongoing prosecution history, including without limitation Office Actions, Amendments, Remarks, and any other potnetially relevant documents, Fram et al.
U.S. Appl. No. 14/095,123, filed Dec. 3, 2013 including its ongoing prosecution history, including without limitation Office Actions, Amendments, Remarks, and any other potentially relevant documents, Reicher et al.
U.S. Appl. No. 14/081,255, filed Nov. 15, 2013 including its ongoing prosecution history, including without limitation Office Actions, Amendments, Remarks, and any other potentially relevant documents, Fram et al.
U.S. Appl. No. 14/244,431, filed Apr. 3, 2014 including its ongoing prosecution history, including without limitation Office Actions, Amendments, Remarks, and any other potentially relevant documents, Reicher et al.
U.S. Appl. No. 14/298,806, filed Jun. 6, 2014 including its ongoing prosecution history, including without limitation Office Actions, Amendments, Remarks, and any other potentially relevant documents, Reicher et al.
U.S. Appl. No. 11/942,687, filed Nov. 19, 2007 including its ongoing prosecution history, including without limitation Office Actions, Amendments, Remarks, and any other potentially relevant documents, Reicher, et al.
U.S. Appl. No. 14/043,165, filed Oct. 1, 2013 including its ongoing prosecution history, including without limitation Office Actions, Amendments, Remarks, and any other potentially relevant documents, Reicher, et al.
U.S. Appl. No. 11/944,000, filed Nov. 21, 2007 including its ongoing prosecution history, including without limitation Office Actions, Amendments, Remarks, and any other potentially relevant documents, Reicher, et al.
U.S. Appl. No. 13/768,765, filed Feb. 15, 2013 including its ongoing prosecution history, including without limitation Office Actions, Amendments, Remarks, and any other potentially relevant documents, Reicher, et al.
U.S. Appl. No. 14/687,853, filed Apr. 15, 2015 including its ongoing prosecution history, including without limitation Office Actions, Amendments, Remarks, and any other potentially relevant documents, Reicher et al.
U.S. Appl. No. 14/792,210, filed Apr. 15, 2015 including its ongoing prosecution history, including without limitation Office Actions, Amendments Remarks, and any other potentially relevant documents, Reicher.
Final Office Action dated Jul. 23, 2015 in U.S. Appl. No. 14/095,123.
Interview Summary dated Aug. 27, 2015 in U.S. Appl. No. 14/095,123.
Notice of Allowance dated Aug. 28, 2015 in U.S. Appl. No. 13/768,765.
Notice of Allowability dated Nov. 20, 2015 in U.S. Appl. No. 13/768,765.
Non-Final Office Action from the U.S. Patent anf Trademark Office for U.S. Appl. No. 14/540,830 dated Jan. 17, 2017 (26 pages).
Notice of Allowance from the U.S. Patent and Trademark Office for U.S. Appl. No. 14/540,830 dated Aug. 15, 2017 (11 pages).
Applicant-Initiated Interview Summary from the U.S. Patent and Trademark Office for U.S. Appl. No. 14/540,830 dated Mar. 24, 2017 (5 pages).
Applicant-Initiated Interview Summary from the U.S. Patent and Trademark Office for U.S. Appl. No. 14/540,830 dated Jul. 28, 2017 (5 pages).
Notice of Allowability from the U.S. Patent and Trademark Office for U.S. Appl. No. 14/502,055 dated Sep. 19, 2016 (3 pages).
Notice of Allowability from the U.S. Patent and Trademark Office for U.S. Appl. No. 14/502,055 dated Jul. 14, 2016 (21 pages).
Notice of Allowability from the U.S. Patent and Trademark Office for U.S. Appl. No. 14/502,055 dated Jun. 27, 2016 (2 pages).
Notice of Allowance from the U.S. Patent and Trademark Office for U.S. Appl. No. 14/502,055 dated Jun. 2, 2016 (10 pages).
Non-Final Office Action from the U.S. Patent anf Trademark Office for U.S. Appl. No. 14/502,055 dated Jan. 20, 2016 (9 pages).
Applicant-Initiated Interview Summary from the U.S. Patent and Trademark Office for U.S. Appl. No. 14/502,055 dated Apr. 14, 2016 (8 pages).
Notice of Allowance from the U.S. Patent and Trademark Office for U.S. Appl. No. 14/095,123 dated Mar. 30, 2017 (10 pages).
Non-Final Office Action from the U.S. Patent anf Trademark Office for U.S. Appl. No. 14/095,123 dated Feb. 23, 2016 (14 pages).
Notice of Allowability from the U.S. Patent and Trademark Office for U.S. Appl. No. 14/081,225 dated Oct. 21, 2016 (2 pages).
Notice of Allowance from the U.S. Patent and Trademark Office for U.S. Appl. No. 14/081,225 dated Sep. 2, 2016 (11 pages).
Non-Final Office Action from the U.S. Patent anf Trademark Office for U.S. Appl. No. 14/081,225 dated Mar. 10, 2016 (23 pages).
Notice of Allowability from the U.S. Patent and Trademark Office for U.S. Appl. No. 14/244,431 dated Nov. 16, 2016 (4 pages).
Notice of Allowance from the U.S. Patent and Trademark Office for U.S. Appl. No. 14/244,431 dated Aug. 18, 2016 (8 pages).
Non-Final Office Action from the U.S. Patent anf Trademark Office for U.S. Appl. No. 14/244,431 dated Mar. 18, 2016 (15 pages).
Applicant-Initiated Interview Summary from the U.S. Patent and Trademark Office for U.S. Appl. No. 14/244,431 dated Jun. 17, 2016 (3 pages).
Notice of Allowance from the U.S. Patent and Trademark Office for U.S. Appl. No. 14/298,806 dated Apr. 12, 2017 (10 pages).
Non-Final Office Action from the U.S. Patent anf Trademark Office for U.S. Appl. No. 14/298,806 dated Feb. 16, 2016 (16 pages).
Final Office Action from the U.S. Patent anf Trademark Office for U.S. Appl. No. 14/298,806 dated Jul. 21, 2016 (18 pages).
Notice of Allowance from the U.S. Patent and Trademark Office for U.S. Appl. No. 11/944,000 dated Jan. 30, 2017 (12 pages).
Non-Final Office Action from the U.S. Patent anf Trademark Office for U.S. Appl. No. 11/944,000 dated Jul. 15, 2016 (13 pages).
Non-Final Office Action from the U.S. Patent anf Trademark Office for U.S. Appl. No. 11/944,000 dated Oct. 5, 2012 (11 pages).
Interview Summary from the U.S. Patent and Trademark Office for U.S. Appl. No. 11/944,000 dated Feb. 4, 2011 (3 pages).
Patent Board Decision from the U.S. Patent and Trademark Office for U.S. Appl. No. 11/944,000 dated Mar. 23, 2016 (8 pages).
Notice of Allowance from the U.S. Patent and Trademark Office for U.S. Appl. No. 13/768,765 dated Jul. 28, 2016 (9 pages).
Examiner-Interview Summary from the U.S. Patent and Trademark Office for U.S. Appl. No. 13/768,765 dated Aug. 28, 2015 (1 page).
Notice of Allowability from the U.S. Patent and Trademark Office for U.S. Appl. No. 14/687,853 dated Jun. 2, 2016 (4 pages).
Notice of Allowance from the U.S. Patent and Trademark Office for U.S. Appl. No. 14/687,853 dated Feb. 25, 2016 (12 pages).
Non-Final Office Action from the U.S. Patent anf Trademark Office for U.S. Appl. No. 14/687,853 dated Aug. 13, 2015 (42 pages).
Non-Final Office Action from the U.S. Patent anf Trademark Office for U.S. Appl. No. 13/477,853 dated Dec. 11, 2013 (9 pages).
Applicant-Initiated Interview Summary from the U.S. Patent and Trademark Office for U.S. Appl. No. 12/857,915 dated Jul. 3, 2014 (1 page).
Examiner-Interview Summary from the U.S. Patent and Trademark Office for U.S. Appl. No. 12/891,543 dated Nov. 14, 2013 (1 page).
Applicant-Initiated Interview Summary from the U.S. Patent and Trademark Office for U.S. Appl. No. 14/179,328 dated Dec. 11, 2014 (3 pages).
Notice of Allowability from the U.S. Patent and Trademark Office for U.S. Appl. No. 13/572,397 dated Jun. 29, 2015 (2 pages).
Interview Summary from the U.S. Patent and Trademark Office for U.S. Appl. No. 11/179,384 dated Feb. 18, 2009 (2 pages).
Interview Summary from the U.S. Patent and Trademark Office for U.S. Appl. No. 11/179,384 dated Sep. 24, 2008 (4 pages).
Notice of Allowance from the U.S. Patent and Trademark Office for U.S. Appl. No. 13/477,853 dated Aug. 15, 2014 (5 pages).

(56) References Cited

OTHER PUBLICATIONS

Final Office Action from the U.S. Patent anf Trademark Office for U.S. Appl. No. 13/477,853 dated Jun. 13, 2014 (13 pages).
Applicant-Initiated Interview Summary from the U.S. Patent and Trademark Office for U.S. Appl. No. 13/477,853 dated Mar. 14, 2014 (3 pages).
Notice of Allowance from the U.S. Patent and Trademark Office for U.S. Appl. No. 11/265,979 dated May 13, 2011 (14 pages).
Examiner-Interview Summary from the U.S. Patent and Trademark Office for U.S. Appl. No. 13/171,081 dated Sep. 4, 2013 (1 page).
Non-Final Office Action from the U.S. Patent anf Trademark Office for U.S. Appl. No. 14/792,201 dated May 3, 2017 (18 pages).
Final Office Action from the U.S. Patent anf Trademark Office for U.S. Appl. No. 14/792,201 dated Nov. 13, 2017 (15 pages).
Applicant-Initiated Interview Summary from the U.S. Patent and Trademark Office for U.S. Appl. No. 14/792,201 dated Feb. 22, 2018 (4 pages).
Notice of Allowance from the U.S. Patent and Trademark Office for U.S. Appl. No. 12/870,645 dated Sep. 13, 2011 (8 pages).
Patent Board Decision from the U.S. Patent and Trademark Office for U.S. Appl. No. 11/942,687 dated Dec. 22, 2017 (13 pages).
Non-Final Office Action from the U.S. Patent anf Trademark Office for U.S. Appl. No. 11/942,687 dated Mar. 13, 2014 (23 pages).
Final Office Action from the U.S. Patent anf Trademark Office for U.S. Appl. No. 11/942,687 dated Jan. 5, 2015 (7 pages).
Interview Summary from the U.S. Patent and Trademark Office for U.S. Appl. No. 11/942,687 dated Jun. 10, 2011 (3 pages).
Non-Final Office Action from the U.S. Patent anf Trademark Office for U.S. Appl. No. 15/475,930 dated Jan. 10, 2018 (1 pages).
Non-Final Office Action from the U.S. Patent and Trademark Office for U.S. Appl. No. 14/792,201 dated Jul. 20, 2018 (16 pages).

\* cited by examiner

ATTRIBUTES

| | 301↓ CONSENT | 302↓ REFERRAL | 303↓ SCREENING | 304↓ REGISTRATION | 305↓ EXAM | 306↓ ID | | | |
|---|---|---|---|---|---|---|---|---|---|
| 312→ SECURITY | C | O | M | M | M | C | ○ | ○ | ○ |
| 314→ LINKS | | | Link -> M | | | | ○ | ○ | ○ |
| 316→ SERIES | CNST | REFL | SCRN | RGST | EXM | ID | ○ | ○ | ○ |
| 318→ FILE TYPE | DOC | DOC | DOC | DOC | IMG | IMG | | | |
| | ○ | ○ | ○ | ○ | ○ | ○ | | | |
| | ○ | ○ | ○ | ○ | ○ | ○ | | | |
| | ○ | ○ | ○ | ○ | ○ | ○ | | | |

310

Legend

| | |
|---|---|
| O | Open |
| C | Confidential |
| M | Medical |
| Link -> M | Link to Medical Images |
| CNST | Consent Form |
| REFL | Referral Form |
| SCRN | Screening Form |
| RGST | Registration Form |
| EXM | Exam Form |
| ID | Patient Identification |
| IMG | Medical Image |
| DOC | Medical Document |

FIG. 7

AUTOMATED DOCUMENT FILING

CROSS-REFERENCE TO RELATED APPLICATIONS

This application is a continuation of U.S. patent application Ser. No. 11/944,027, filed Nov. 21, 2007, and titled "Automated Document Filing," which application claims the benefit of U.S. Provisional Application No. 60/867,071, filed Nov. 22, 2006. Each of the above identified applications is hereby incorporated by reference in its entirety herein.

BACKGROUND OF THE INVENTION

Field of the Invention

The invention relates to management of medical forms.

Description of the Related Art

Medical documents are often scanned and processed into an electronic format for easy filing and recording of a patient's medical history. These medical documents encompass a variety of medical forms, such as medical registration forms, consent forms, and screening forms, for example. Depending on the type of medical document, the documents may have different user access rights, security rights, and modes of display.

SUMMARY OF THE INVENTION

In one embodiment, a computerized method of assigning attributes to medical forms comprises receiving an electronic copy of a form associated with a patient, determining one or more form types associated with the medical form from a plurality of form types, the plurality of form types comprising one or more of referral, medical record release, consent, and screening, accessing an attribute data structure comprising indications of each of the plurality of form types and one or more attributes associated with each respective form type, selecting attributes of the attribute data structure associated with the determined one or more form types, and storing the electronic copy of the form in a storage location associated with one or more of the selected attributes.

In one embodiment, a computerized system of organizing medical forms completed by a plurality of patients comprises a storage device storing an attribute data structure comprising indications of attributes associated with respective medical form types, the attributes comprising at least a security attribute and a document type attribute for each of the medical form types, an input interface configured to receive a digital representation of a medical-related form, the medical-related form comprising information associated with a patient, and a document management module configured to determine one or more form types associated with the medical-related form and to store the digital representation of the medical-related form with data indicating the attributes from the attribute data structure associated with the determined one or more form types.

In one embodiment, a computer-readable storage medium comprises software code configured to perform the method of storing a data structure on a storage device, the data structure comprising an indication of one or more document types and one or more attributes that are associated with respective of the document types, receiving an indication of a document type associated with an electronic document, selecting one or more attributes associated with the indicated document type in the data structure, and associating the selected one or more attributes with the electronic document.

In one embodiment, a computerized method of viewing medical forms comprises receiving an indication of an electronic form that a user of a computing system desires to view, accessing attribute data associated with the electronic form, the attribute data comprising at least a security attribute and a document type attribute, determining one or more display parameters for viewing the electronic form based on the attribute data, and generating a user interface comprising a depiction of the electronic form according to the determined display parameters.

BRIEF DESCRIPTION OF THE DRAWINGS

FIG. 3 illustrates an attribute data structure comprising data that indicates associations between respective series and their corresponding attributes.

FIG. 7 is one embodiment of a graphical user interface that may be used to select electronic documents and assign series attributes to the selected documents.

DETAILED DESCRIPTION OF CERTAIN EMBODIMENTS

Embodiments of the invention will now be described with reference to the accompanying figures, wherein like numerals refer to like elements throughout. The terminology used in the description presented herein is not intended to be interpreted in any limited or restrictive manner, simply because it is being utilized in conjunction with a detailed description of certain specific embodiments of the invention. Furthermore, embodiments of the invention may include several novel features, no single one of which is solely responsible for its desirable attributes or which is essential to practicing the inventions herein described.

As used herein, the terms "medical forms," "forms," and "documents" are defined to include any forms related to medical information, images, and patient information. As non-limiting examples, the terms may include, but are not limited to, image screening forms, patient information forms, insurance information forms, information forms for respective exam types, consent forms, and many other types of medical-related forms. Medical forms may be hard copy forms and/or electronic forms of various formats, such as PDF, DOC, XLS, HTML, XML, and various other formats.

As used herein, the terms "series type," "series," and "document type" are used to describe a category of forms. In one embodiment, a series is representative of the subject matter of forms associated with the series, such as screening, registration, and/or consent forms. In other embodiments, a series associated with a document indicates other characteristics of the document, such as a form provider or medical facility.

As used herein, the term "attribute" includes, but is not limited to an indicator of a characteristic of each form in of a respective series. In one embodiment, each series is associated with one or more attributes, and the attributes of a respective series are associated with documents in the respective series. Series attributes may comprise information indicating a security level associated with a document, a storage location of a document, a viewer associated with a document, a link to another related document, and/or a document type of a document. Depending on the embodiment, attributes may include indications of other characteristics of forms and/or the information contained in the forms.

Document Management

Figure 1A:
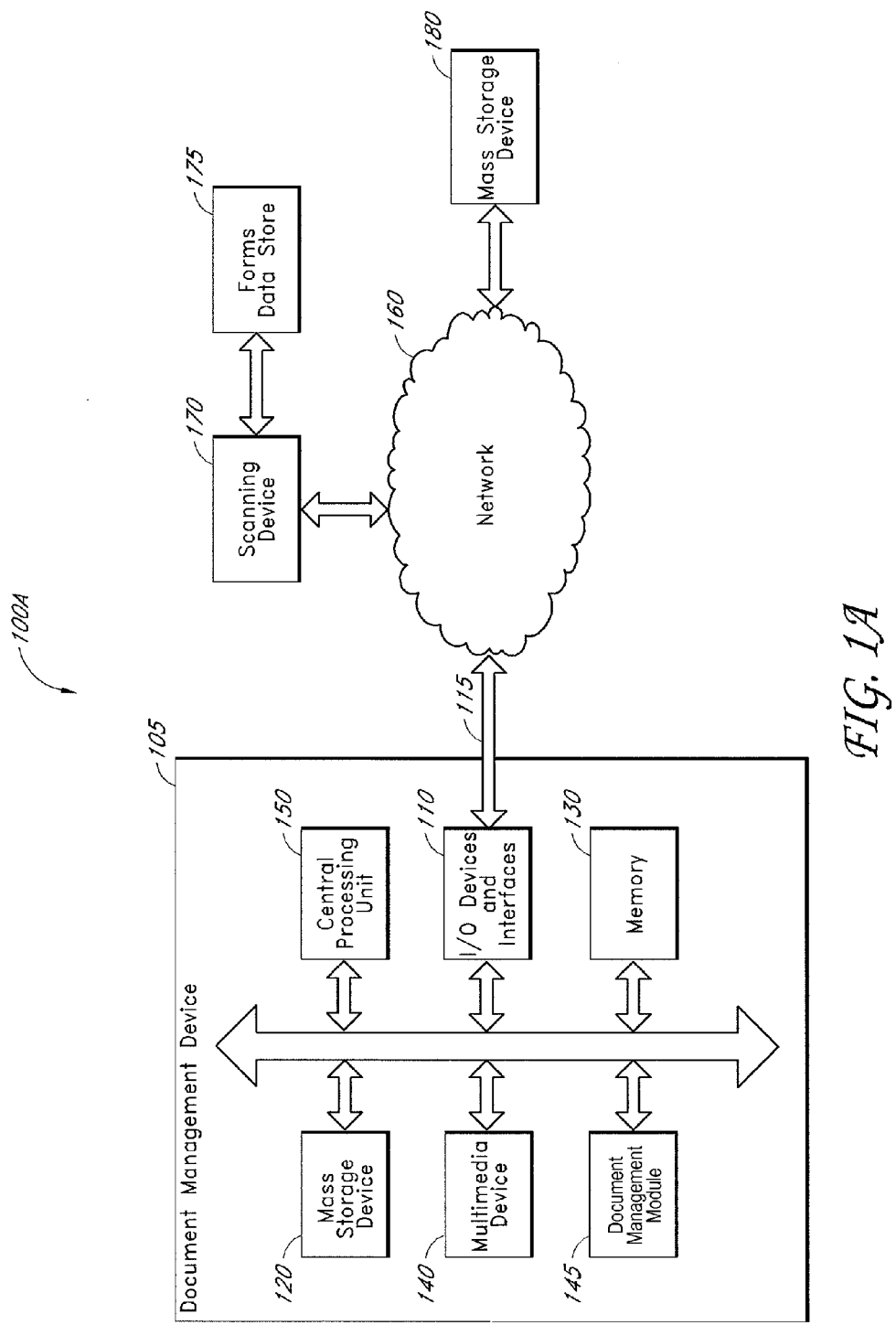
FIG. 1A is a block diagram of a computing system comprising a document management device in communication with a network and various networked devices.

FIG. 1A is a block diagram of a computing system 100A comprising a document management device 105 in communication with a network 160 and various networked devices. The computing system 100A may be used to implement certain systems and methods described herein. Depending on the embodiment, the functionality described below with reference to certain components and modules of the computing system 100A may be combined into fewer components and modules or further separated into additional components or modules.

The exemplary document management device 105 comprises a memory 130, such as random access memory (RAM) for temporary storage of information and a read only memory (ROM) for permanent storage of information, and a mass storage device 120, such as a hard drive, diskette, or optical media storage device. The mass storage device 120 may comprise one or more hard disk drive, optical drive, networked drive, or some combination of various digital storage systems. The document management device 105 also comprises a central processing unit (CPU) 150 for computation. Typically, the modules of the document management device 105 are in data communication via one or more standards-based bus system. In different embodiments, the standards based bus system could be Peripheral Component Interconnect (PCI), Microchannel, SCSI, Industrial Standard Architecture (ISA) and Extended ISA (EISA) architectures, for example.

The document management device 105 is generally controlled and coordinated by operating system software, such as the Windows 95, 98, NT, 2000, XP, Vista, or other compatible operating systems. In Macintosh systems, the operating system may be any available operating system, such as Mac OS X. In other embodiments, the document management device 105 may be controlled by a proprietary operating system. Conventional operating systems control and schedule computer processes for execution, perform memory management, provide file system, networking, and I/O services, and provide a user interface, such as a graphical user interface ("GUI"), among other things.

The exemplary document management device 105 includes one or more of commonly available input/output (I/O) devices and interfaces 110, such as a keyboard, mouse, touchpad, and printer. In one embodiment, the I/O devices and interfaces 110 include one or more display devices, such as a monitor, that allows the visual presentation of data to a user. More particularly, display devices provide for the presentation of GUIs, application software data, and multimedia presentations, for example. In one embodiment, a GUI includes one or more display panes in which medical images and/or medical forms may be displayed. The document management device 105 may also include one or more multimedia devices 140, such as speakers, video cards, graphics accelerators, and microphones, for example.

In the embodiment of FIG. 1A, the I/O devices and interfaces 110 provide a communication interface to various external devices. In the embodiment of FIG. 1A, the document management device 105 is in data communication with a network 160, such as a LAN, WAN, or the Internet, for example, via a communication link 115. The network 160 may be coupled to various document management devices and/or other electronic devices. In the exemplary embodiment of FIG. 1A, the network 160 is in data communication with a forms data store 175, a scanning device 170, and a mass storage device 180. In other embodiments, the scanning device 170 may be locally coupled to the document management device 105. In addition to the devices that are illustrated in FIG. 1A, the network 160 may facilitate communications with other computing, imaging, and storage devices.

The forms data store 175 comprises a plurality of hardcopy and/or electronic documents, some of which comprise user editable fields configured to receive patient information. Patients may be asked to complete one or more forms that ask for patient biographical information, insurance information, exam information (e.g. exam modality), consent, or other information. Exemplary forms may include a radiology screening form, a patient information form, an insurance information form, an exam type form, various patient consent forms, and many other types of medical forms.

The scanning device 170 comprises an electronic device that digitizes a form from the forms data store 175. Exemplary scanning devices may include a flatbed scanner, a hand scanner, or a drum scanner. In one embodiment, the scanning device 170 may comprise optical character recognition (OCR) software to translate images of handwritten or typewritten text into machine-editable text. In another embodiment, the scanning device 170 may analyze and decode document type indicators on scanned documents, such as a barcode that indicates a document type. As noted below, in certain embodiments forms may be electronic such that the scanning device 170 may not be necessary.

In one embodiment, the mass storage device 120, 180 may be any device that electronically stores information. Exemplary devices include, but are not limited to a hard disk drive, a flash memory based drive, a thumb drive, and disc-based storage mediums, such as a CD or DVD, for example. In one embodiment, these devices may be networked in series or in parallel with each other and may comprise storage area networks (SAN) for networking with the document management device 105. Depending on the embodiment, the mass storage device 120, 180 may comprise redundant array of independent drives (RAID) for increased data reliability or I/O performance, or both.

In the embodiment of FIG. 1A, the document management module 145 is configured to associate series attributes with one or more electronic documents, such as scanned documents or electronically completed documents. In one embodiment, the document management module 145 provides a user interface that may be used to provide an indication of one or more series associated with an electronic document. In another embodiment, this module receives information regarding document attributes from another source. In other embodiments, the document management module 145 comprises document detection intelligence that determines a type of document and/or series for an electronic document. After determining a series associated with a document, the document management module 145 determines attributes for the determined series and associates those attributes with the electronic document. The document attributes associated with the electronic document may then be used to control user's rights to the document, indicate a type of viewer associated with the document, indicate a storage location for the document, indicate a type of the electronic document, and/or indicate when a document is to be stored (such as differentiating forms that require user completion from those that are stored with a patient's record without first requiring completion), for example.

Figure 1B:
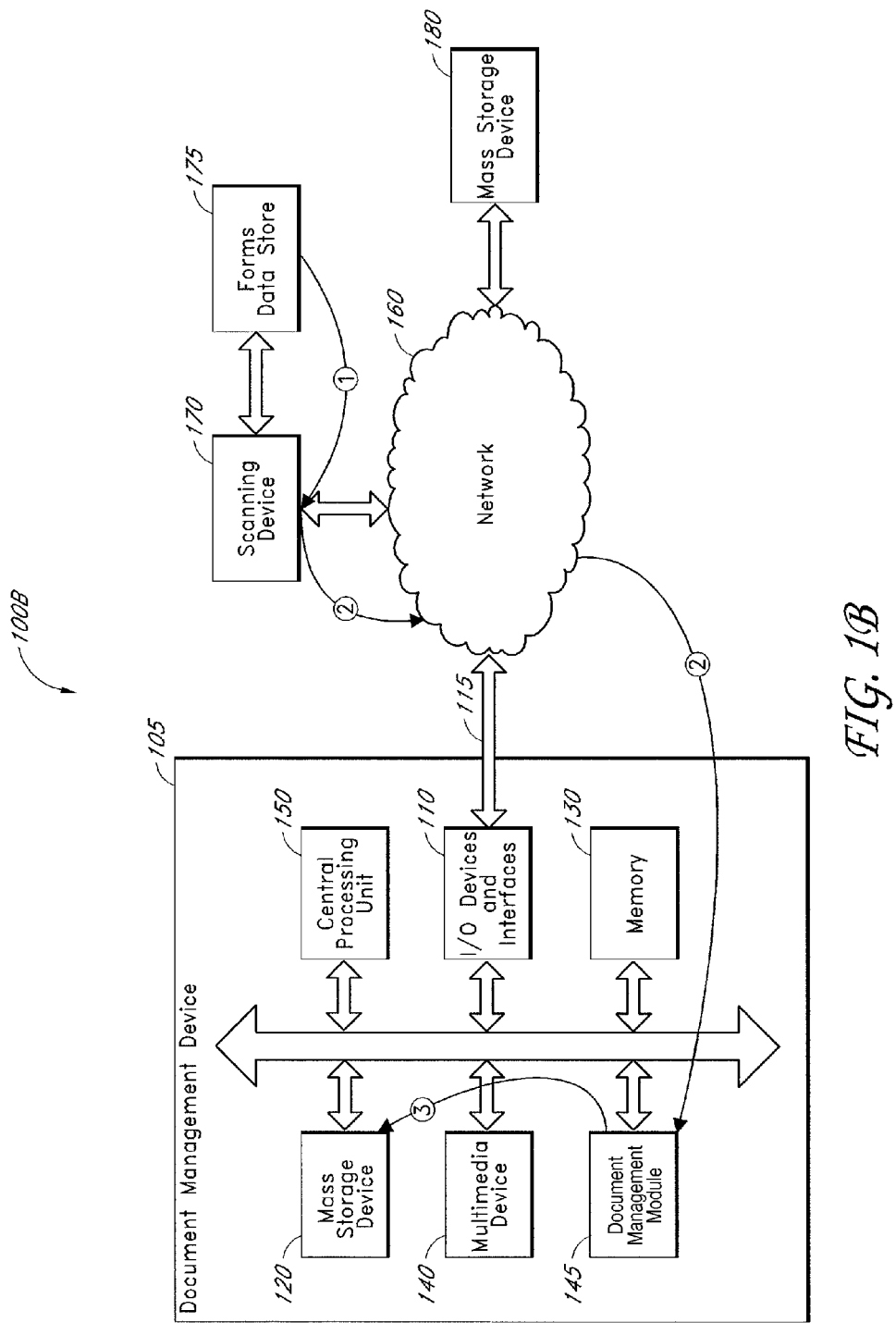
FIG. 1B is a block diagram illustrating one embodiment of a computing system comprising a document management device in communication with a network and various networked devices.

FIG. 1B is a block diagram illustrating one embodiment of a computing system 100B comprising a document management device 105 in communication with a network 160 and various networked devices. The computing system 100B may be used to implement certain systems and methods described herein. In the embodiment of FIG. 1B, an exemplary temporal flow of operations is indicated by the circled numerals 1-3 and is described in further detail below. Depending on the embodiment, certain steps may be removed and additional steps may be added.

In step one of FIG. 1B, the scanning device 170 receives and scans one or more physical documents from the forms data store 175 in order to convert the physical documents into corresponding electronic documents. For example, the scanning device 170 may receive a plurality of forms on a sheetfeeder, scan the forms, and create digital representations of the scanned forms in one or more of many available digital formats, including PDF, PNG, JPG, GIF, and TIFF, for example.

In another embodiment, the forms data store 175 comprises electronic forms comprising medical-related information that do not require scanning. In this embodiment, the forms data store 175 may be accessed directly by the document management device 105, such as via the network 160 or a local area network, for example.

In step two of FIG. 1B, the electronic documents, or at least a representation of the electronic documents, are accessible by the document management device 105. The document management module 145 may then receive or determine a series of each electronic document so that attributes of the determined series may be associated with the document. In one embodiment, a user of the document management module 145 views at least a portion of the electronic documents in order to determine a series of respective documents. The user may then select one or more series via a user interface provided by the document management device 105. In another embodiment, the document management module 145 and/or scanning device 170 are configured to determine a series of certain electronic documents based on a visual indicator of the electronic documents, such as a document title, header, footer, document number, etc. that are recognized in the electronic documents, such as by using OCR recognition of a scanned document.

In step three, the document management module 145 determines those attributes associated with the determined series of an electronic document and associates the series attributes with the specific document. In one embodiment, the document management module 145 accesses one or more data structures comprising associations between respective series and attributes, such as attributes indicating security/access rights, document type, viewer information, and/or form storage information, for example. The electronic document, along with the corresponding attributes, may then be stored in the mass storage device 120 and/or any other external storage device, such as the mass storage device 180 and/or a storage device of an electronic medical records ("EMR") system (not shown), for example.

Figure 2:
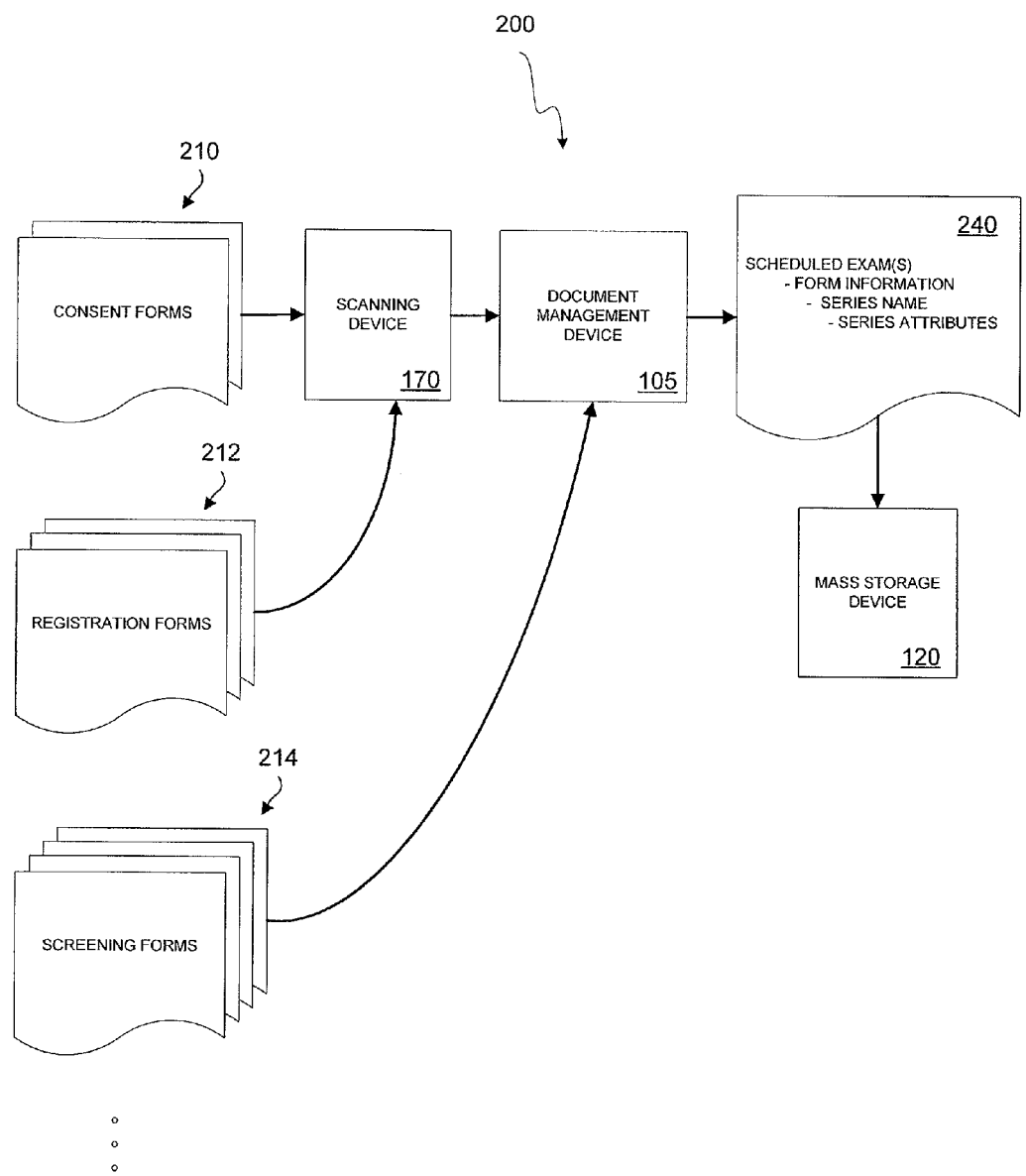
FIG. 2 is a data flow chart illustrating the movement of physical and electronic documents through a document management system.

FIG. 2 is a data flow chart 200 illustrating the movement of physical and electronic documents through a document management system. Starting from the scanning device 170 in FIG. 2, physical forms 210 and 212 are scanned into an electronic format and sent to, or otherwise accessed by, the document management device 105. In the embodiment of FIG. 2, the screening forms 214 comprise electronic forms that are directly transmitted to, or otherwise accessed by, the document management device 105, such as via a local and/or network connection to the document management device 105.

When the document management module 145 has received an electronic form, the document management module 145 associates attributes to the form that direct further automated storage and display rules. For example, a user of the document management device 105 may view at least a portion of the form in a user interface provided by the device 105 and make a determination as to a "series" associated with the form. When the form is included in a particular "series", the attributes of that series can determine how the form is stored, when it is stored, how it is displayed, and/or it's level of security, for example. Alternatively, the device 105 may automatically associated attributes to the form based on one or more visually detectable characteristics of the form. Advantageously, certain series are associated with one or more attributes so that forms in a particular series may inherit the attributes of that particular series. As discussed above, series attributes may indicate a document type, a link to another documents, and/or a security level of a particular document. The form attributes may be included in a header portion of the digital file or a separate file associated with the digital file, for example.

Form 240 of FIG. 2 illustrates exemplary attribute information that may be associated with the electronic document. As illustrated in FIG. 2, the form 240 is associated with a scheduled exam, which may include various types of patient information, such as patient name, address, contact information, medical record number, social security number, etc. In other embodiments, the form 240 is not associated with a particular exam, but is generally associated with a patient, such as via a patient identification number or social security number. The form 240 also includes an indication of the series to which the form has been associated, e.g., either automatically by the document management device 105 or manually by a user viewing at least a portion of the form. The form 240 also includes zero or more attributes associated with the form, such as those attributes that are automatically associated with the form based on an indicated series of the form. In one embodiment, the series name is not include as part of the form information; instead, only the attributes associated with the form's series are assigned to the form.

After associating the appropriate attributes to the digital forms 210, 212, 214, the forms may be stored in one or more data stores, such as the mass storage device 120, 180. In one embodiment, the processed forms may be stored in one or more folders based on one or more of the attributes. For example, one or more attributes may indicate a folder to which a corresponding form should be stored. In this embodiment, all of the forms in a particular series may be automatically stored in a series-specific folder. In one embodiment, a patient's medical records comprises folders for certain forms, such as a consent folder for storage of executed consent forms. By accessing the document type attribute of forms, consent forms may be identified and the document management module 145 may be configured to automatically move the consent form to the consent folder for the corresponding patient.

FIG. 3 illustrates an attribute data structure 310 comprising data that indicates associations between respective series and their corresponding attributes. In one embodiment, the document management module 145 may determine attributes to associate with a particular form by accessing the data structures 310. FIG. 3 also illustrates a legend 320 that indicates the meaning of symbols used in the data structure 310. Although exemplified in the form of a table, the intent is not to limit the data structure that may be employed to create associations or links between forms, attributes, and other links to such various items as exam types, facilities, insurance information, for example.

The exemplary data structure 310 comprises attribute data associated with six exemplary series. More particularly, the data structure 310 comprises a consent series column 301, a referral series column 302, a screening series column 303, a registration series column 304, an exam series column 305, and an identification series column 306. Each of the series may be associated with one or more attributes, such as security attributes indicated in row 312, link attributes in row 314, series type attributes in row 316, and/or file type attributes in row 318. For example, the exemplary data structure 310 indicates that documents in the referral series should be associated with an open security level, a REFL symbol indicating that the document is a referral document, and that the documents are medical documents (rather than medical images). In one embodiment, the file type of a form (e.g., row 318) indicates a particular viewer or class of viewer that is used by a viewer of the form. For example, medical documents may be opened in a first viewer, such as a word processing or portable document viewer, and medical images may be opened in a second viewer, such as a viewer of radiology imaging software. Depending on the embodiment, the data structure 310 may comprise additional series attributes and/or different attributes associated with respective series. For example, additional attributes may include information regarding image size and image resolution, for example.

FIG. 3 illustrates three security attributes, namely, open, confidential, and medical. Depending on the embodiment, fewer or additional security attributes may be associated with forms. In one embodiment, the open security level indicates that an associated document may be viewed by any user of the system, including clerical workers and medical professionals; the confidential security level indicates that viewers with a confidential clearance may view the document; and the medical security level indicates that only medical personnel, such as a family doctor may view the document.

The exemplary data structure 310 indicates a link attribute for screening series 303. In one embodiment, link attributes are used to associate two or more types of forms and/or specific forms. Using a link attribute may enable form(s) related to a requested form to be automatically opened in response to a link attribute associated with a requested form. In one embodiment, when two or more forms are linked together, both forms may be viewed at the same time when either form is selected. For example, it may be advantageous to have a patient screening form linked to medical images associated with a scheduled exam, so that when the patient screening form is accessed the medical images are opened, listed for easy access by the user, or otherwise brought to the attention of the user.

The file type attributes of FIG. 3 include medical document (DOC) and medical image (IMG) file types. In one embodiment, files of the same file type are filed in the same folder on the mass storage device 120, 180. For example, medical documents and medical images for a particular scheduled exam may be filed in separate folders. In one embodiment, a patient's scheduled exam may include a plurality of files and each of the files may be sorted and stored in different folder structures depending on the document type of the files(s).

In one embodiment, document types and/or other attributes of a document may indicate a mode of display. For example, certain types of documents may be displayed in a new display container to illustrate and isolate particular features of the document without interrupting the user's eyes from viewing something else, while other types of documents are opened in a currently active display container.

Figure 4:
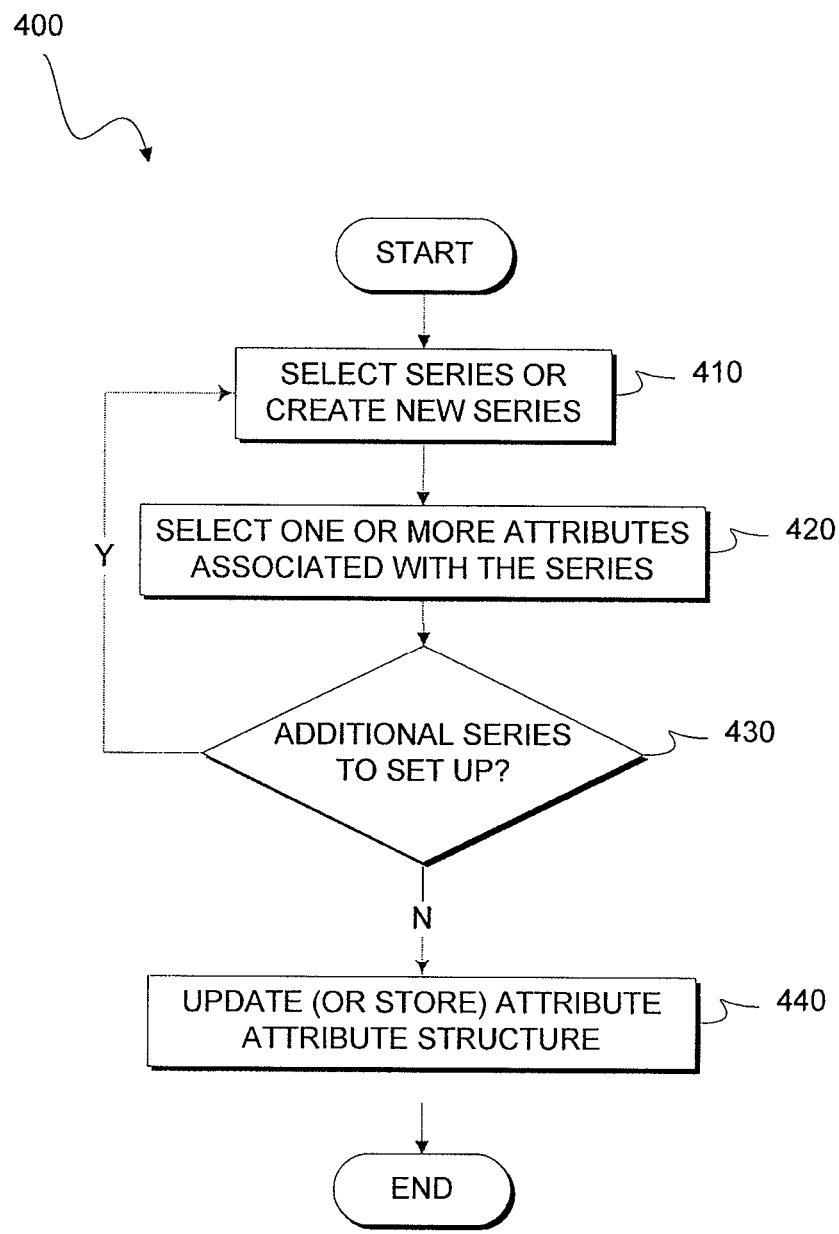
FIG. 4 is a flowchart illustrating one embodiment of a method of establishing attributes associated with respective series.

FIG. 4 is a flowchart illustrating one embodiment of a method of establishing attributes associated with respective series. In one embodiment, the method of FIG. 4 is performed by an administrator that has rights to establish new series and/or attributes associated with existing series. For example, a user interface may be presented to the administrator in order to allow selection of attributes for association with respective series. Depending on the embodiment, the method of FIG. 4 may include fewer or additional blocks, and the blocks may be performed in a different order than as illustrated.

Beginning in block 410, an existing series is selected or a new series is created. For example, the user may create a consent series that is associated with attributes that should be associated with consent forms. Alternatively, the user may select an existing series that may already have one or more associated attributes so that the attributes that are currently associated with the series may be edited.

Next, in block 420 one or more attributes to be associated with the selected series (block 410) are selected by the user. For example, the user may select one or more of a security, link, series, file storage location, file type, and/or any other available attribute to be associated with the selected series. Depending on the embodiment, other attributes may also be available for selection in block 420.

Moving to block 430, the user determines if additional series are to be set up and/or modified to be associated with different attributes. If additional series are to be added and/or modified, the method returns to blocks 410 and then 420.

In block 440, the attributes associated with respective series (e.g., blocks 410-430) are stored in an attribute data structure. As discussed above, the attribute data structure may be accessed by the document management module 145 in order to determine attributes to be associated with a particular electronic document, such as a scanned form.

Figure 5:
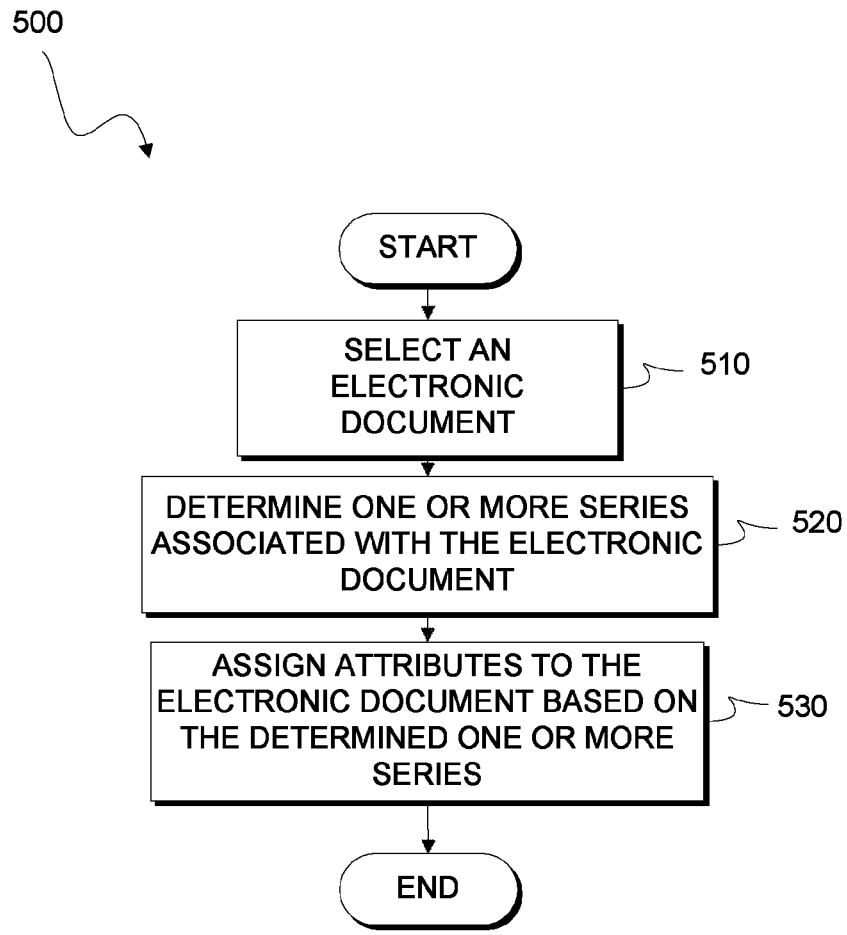
FIG. 5 is a flow chart illustrating one embodiment of a method of assigning attributes to electronic documents.

FIG. 5 is a flow chart illustrating one embodiment of a method of assigning attributes to electronic documents. Depending on the embodiment, the method of FIG. 5 may include fewer or additional blocks and the blocks may be performed in a different order than illustrated.

Beginning in block 510, an electronic document is selected. Selection of an electronic document may comprise selecting an electronic document from a list of electronic documents, such as in a folder of an electronic file structure. Alternatively, selection of an electronic document may comprise scanning a physical document such that a representation of at least a portion of the scanned document is presented to the user in a user interface. In other embodiments, electronic documents may be selected from other sources, such as a networked mass storage device or an EMR system. In one embodiment, batch processing may be used to select a series of electronic documents.

Moving to block 520, the document management module 145 determines one or more series that are associated with the electronic document. In one embodiment, a user of the document management device 105 selects the one or more series associated with the selected electronic document. In one embodiment, a list of available series are presented to the user and the user selects one or more series using an input device, such as a keyboard and/or mouse. In other embodiments, one or more series may be selected using any other means. In one embodiment, a series may be associated with only a single electronic document, while in other embodiments a series may be associated with a group of electronic documents. In another embodiment, the document management system 105 may analyze and decode series indicators on the electronic document, such as a barcode that indicates a series type.

Next, in block 530, the document management module 145 accesses the attribute data structure in order to determine one or more attributes to be associated with the electronic document. The document manager module 145 then associates the appropriate attributes to the electronic document so that the attributes are accessible to authorized users subsequently requesting access to the electronic document. For example, if the user selects the referral series in block 520, those attributes associated with the referral series are associated with the electronic document. In one embodiment, the attributes are stored in a header portion of the electronic document. In another embodiment, the attributes are stored in an index comprising an indication of the electronic document and/or the electronic document storage location, as well as the attributes associated with the electronic document. In other embodiments, the attributes associated with an electronic document may be stored in any other suitable format, such as a separate file that is stored with the electronic document.

After associating attributes with the electronic document, the document may be filed in a specific folder based on one or more attributes of the document. These attributes may indicate that the electronic document should be stored in a particular folder associated with a particular patient and/or a particular scheduled exam of the patient.

Figure 6:
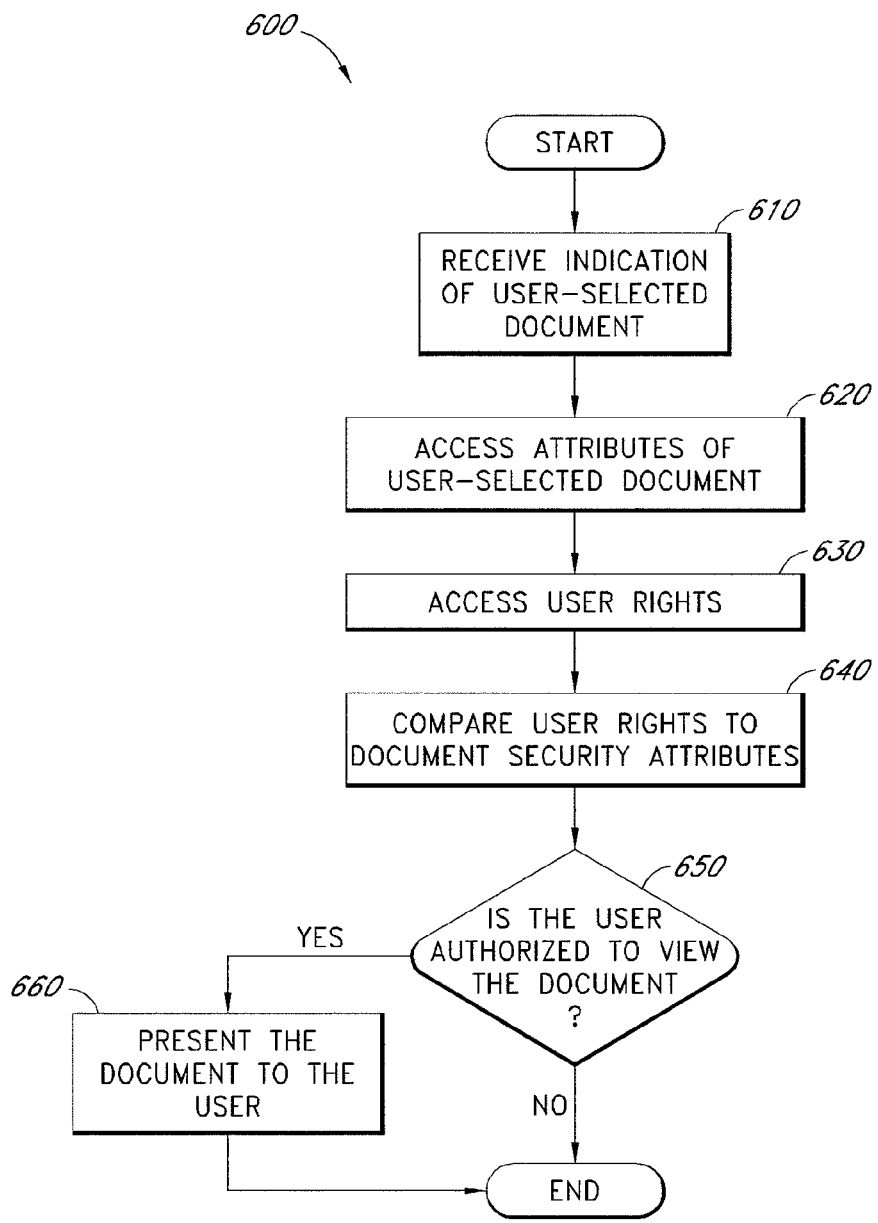
FIG. 6 is a flowchart illustrating one embodiment of a method of accessing an electronic document having associated attributes.

FIG. 6 is a flowchart illustrating one embodiment of a method of accessing an electronic document having associated attributes. Depending on the embodiment, the method of FIG. 6 may include fewer or additional blocks and the blocks may be performed in a different order than is illustrated.

Beginning in block 610, the document management device 105 receives an indication of a user selected document. For example, a user of the document management device 105 requests an electronic document for viewing via medical records software. Alternatively, a remote user, such as a user in communication with the document management device 105 via the network 160 may request access to a document stored on the document management device 105. In other embodiments, the documents and their associated attributes are stored remote to the document management device 105. In these embodiments, the indication of a user selected document may be received by a computing device that stores the particular requested document and/or controls access to the electronic documents. Thus, the method of FIG. 6 may be performed by the document management device 105 and/or by another computing device that controls access to electronic documents. For ease of description, the remaining description of FIG. 6 will be described with reference to the document management device 105, with the understanding that references to the document management device 105 should be interpreted to include actions that may be performed by other computing devices that control access to electronic documents.

Moving to block 620, the document management module 105 accesses the attributes of the user selected document. For example, the header information of the document may be accessed in order to determine attributes that are associated with a document.

Continuing to block 630, the requesting user's access rights are determined, such as via an access rights data structure indicating rights associated with respective users. For example, each user may be granted rights to one or more of open, confidential, and/or medical electronic documents.

In block 640, the user rights are compared to any security attributes associated with the electronic document.

Next, in block 650, the document management device 105 determines if the user is authorized to view the requested electronic document. In one embodiment, the determination is based on the comparison of user rights to document security attributes. For example, if the requesting user only has rights to view open electronic documents, the user may be denied access to confidential electronic documents. If the user is determined to have rights to view the requested document, the method continues to block 660 where the electronic document is transmitted to the user, or otherwise made accessible to the user. If, however, the user does not have rights to view the document, the user is not provided access to the electronic document.

Figure 7:
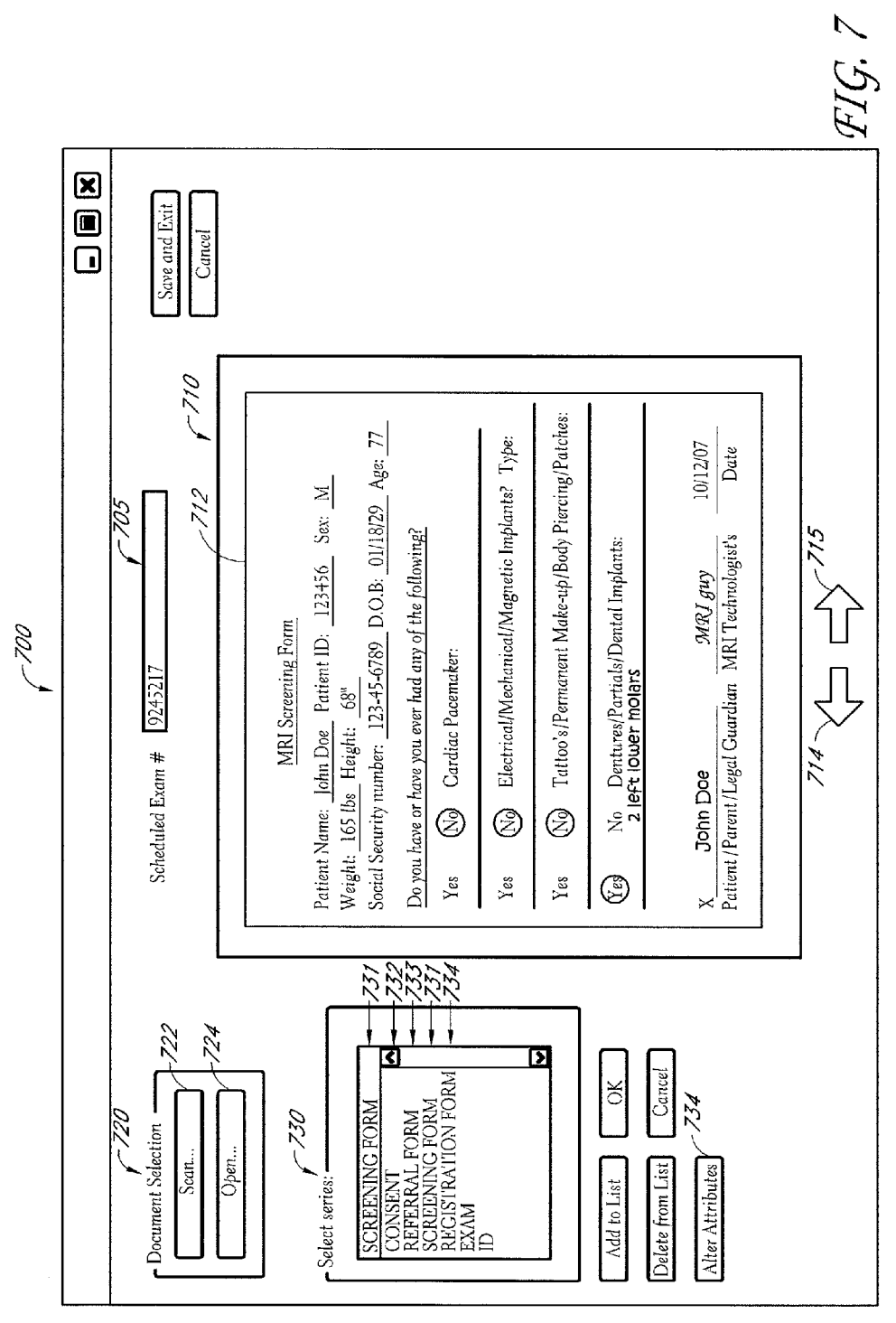

FIG. 7 is one embodiment of a graphical user interface 700 that may be used to select electronic documents and assign series attributes to the selected documents. The embodiment of FIG. 7 may be used to control operation of a scanner and to open electronic documents from a local or remote storage device. The exemplary graphical user interface 700 comprises a document preview pane 710, a document selection pane 720, a series selection pane 730, and a scheduled exam field 705. Depending on the embodiment, the layout of the graphical user interface, the types of input fields, buttons, and checkboxes may be modified.

The patient scheduled exam field 705 may be used to associate an electronic document displayed in preview pane 710 with a particular patient scheduled exam. As noted above, the patient scheduled exam may comprise the patient identification number and one or more attributes associated with the patient.

The document preview pane 710 may be used to view at least a portion of a selected electronic document. Thus, a user may better perceive the content of the selected electronic document by viewing at least a portion of the document in the preview pane 710. Arrows 714, 715 may be used to move to previous or next electronic documents in a directory of a storage device, such as a scanned images folder on a storage device, for example.

The document selection pane 720 may be used to select an electronic document for assigning attributes. In one embodiment, selecting button 724 displays options/parameters to select an electronic form residing on mass storage device 120, 180, while selecting button 722 may indicate that an electronic document should be acquired from a scanner, and may present the user with scanning parameters that may be adjusted prior to scanning documents.

In the embodiment of FIG. 7, the series selection pane 730 is used to select one or more series to be associated with the electronic document depicted in the document preview pane 710. Exemplary series selection pane 700 illustrates several series identifier that may be selected by the user in order to indicate one or more series attributes to be associated with the currently selected electronic document.

Exemplary user interface 700 further comprises an alter attributes button 734 that may be used to alter attributes associated with a series, such as adding and/or removing attributes associated with a series.

The foregoing description details certain embodiments of the invention. It will be appreciated, however, that no matter how detailed the foregoing appears in text, the invention can be practiced in many ways. For example, the above-described document management module 145 may be performed on other types of documents, in addition to medical forms. For example, educational forms and business documents may be analyzed using the described systems. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A method of associating attributes with an electronic medical form, the method comprising:

receiving, at a computing system including one or more computing devices configured with computer executable instructions, a first patient-specific electronic medical form including one or more fields that are filled with information associated with a first patient, the information including at least a first specific patient identifier;

accessing, by the computing system, an electronic data store storing:

indications of a plurality of different electronic form types, wherein each of the plurality of different electronic form types identifies a respective class of electronic medical forms and is not specific to any individual form, and for each respective electronic form type of the plurality of different electronic form types:

an association between the respective electronic form type and a plurality of attributes, at least one of the plurality of attributes comprising a plurality of values, wherein at least one of the plurality of attributes associated with each respective electronic form type indicates a storage location for patient-specific electronic medical forms of the respective electronic form types, wherein at least one of the plurality of attributes associated with each respective electronic form type indicates a security attribute for patient-specific electronic medical forms of the respective electronic form types, wherein the security attribute associated with each respective electronic form type indicates one of a plurality of security attribute values each corresponding to a different level of access, and wherein at least one of the plurality of attributes associated with each respective electronic form type indicates a link attribute for patient-specific electronic medical forms of the respective electronic form types, wherein the link attribute associated with each respective electronic form type indicates one of a plurality of link attribute values each indicating a respective link to a respective linked to electronic medical form;

determining, by the computing system, a first electronic form type of the first patient-specific electronic medical form based on one or more indicia included on the first patient-specific electronic medical form;

identifying, by the computing system and by reference to the electronic data store, the first electronic form type from among the plurality of different electronic form types;

determining, by the computing system and by reference to the electronic data store, a first plurality of attributes associated with the first electronic form type of the first patient-specific electronic medical form;

associating, by the computing system, the first patient-specific electronic medical form with the first plurality of attributes associated with the first electronic form type including a first storage attribute;

identifying, by the computing system and by reference to the first storage attribute, a storage location for the first patient-specific electronic medical form;

initiating storage, by the computing system, of the first patient-specific electronic medical form at the storage location;

receiving, at the computer system, a request to access the first patient-specific electronic medical form;

identifying the linked to electronic medical form by reference to the link attribute value of the link attribute of the first plurality of attributes;

comparing, at the computer system, a first level of access associated with the request with the security attribute value of the security attribute of the first plurality of attributes;

comparing, at the computer system, a second level of access associated with the request with the security attribute value of the security attribute associated with an electronic form type of the linked to electronic medical form;

in response to determining that a user has authorization to access the first patient-specific electronic medical form, retrieving, by the computer system, the first patient-specific electronic medical form;

in response to determining that the user has authorization to access the linked to electronic medical form, automatically retrieving, by the computer system, the linked to electronic medical form;

receiving, at the computing system, a second patient-specific electronic medical form including a second one or more fields that are filled with second information associated with a second patient, the second information including at least a second specific patient identifier;

determining, by the computing system, a second electronic form type of the second patient-specific electronic medical form;

identifying, by the computing system and by reference to the electronic data store, the second electronic form type from among the plurality of different electronic form types;

determining, by the computing system and by reference to the electronic data store, a second plurality of attributes associated with the second electronic form type of the second patient-specific electronic medical form; and associating, by the computing system, the second patient-specific electronic medical form with the second plurality of attributes associated with the second electronic form type, wherein the first electronic form type is the same as the second electronic form type, such that the first plurality of attributes are identical to the second plurality of attributes.

2. The method of claim 1, wherein determining the first electronic form type of the first patient-specific electronic medical form comprises:

automatically determining, by the computing system, the first electronic form type of the first patient-specific electronic medical form.

3. The method of claim 2, wherein the indicia includes one or more visually detectable characteristics that are automatically detectable by the computing system.

4. The method of claim 1, wherein determining the first electronic form type of the first patient-specific electronic medical form comprises:

receiving an input provided by a user of the computing system; and determining, based on the input, the first electronic form type.

5. The method of claim 1, wherein initiating storage of the first patient-specific electronic medical form at the storage location further includes:

initiating storage of the first plurality of attributes associated with the first patient-specific electronic medical form at the storage location.

6. The method of claim 1, further comprising:

scanning, with an optical imaging device in data communication with the computing system, the first patient-specific electronic medical form, wherein said determining the first electronic form type of the first patient-specific electronic medical form comprises analyzing a scanned representation of the first patient-specific electronic medical form.

7. The method of claim 6, further comprising:

performing optical character recognition of the scanned representation of the first patient-specific electronic medical form in order to determine alphanumeric characters in the first patient-specific medical examination form; and parsing the determined alphanumeric characters for a series of characters indicative of the first electronic form type.

8. The method of claim 7, wherein the determined alphanumeric characters are included in at least one of a document title, a document header, or a document footer of the first patient-specific electronic medical form.

9. The method of claim 1, wherein the first patient-specific electronic medical form comprises an electronic document having one or more fields that are filled with electronic data.

10. The method of claim 1, wherein the first electronic form type is selected from a group including at least one of: consent, referral, screening, registration, exam, patient information, or insurance information.

11. The method of claim 1 further comprising:

determining, by the computing system, based on at least one of the first plurality of attributes associated with the first patient-specific electronic medical form and/or the first electronic form type, one or more display parameters for viewing the first patient-specific electronic medical form; and displaying, on an electronic display of the computing system, the first patient-specific electronic medical form according to the determined one or more display parameters.

12. The method of claim 11, wherein the display parameters comprise one or more of a parameter indicating a window for viewing of an electronic copy of the first patient-specific electronic medical form, a parameter indicating a viewer type, and/or a parameter indicating a required security level of a viewer that is required for viewing the electronic copy of the form.

13. The method of claim 1, further comprising:

scanning, with an optical imaging device in data communication with the computing system, the first patient-specific electronic medical form;

identifying, based on information from the optical imaging device, a barcode on the first patient-specific electronic medical form; and accessing a data structure associating barcodes with respective electronic form types, wherein said determining the first electronic form type comprises:

determining, by the computing system, the first electronic form type of the first patient-specific electronic medical form based on an association between the first electronic form type and the identified barcode in the data structure.

14. The method of claim 1, wherein the linked to electronic medical form comprises medical images.

* * * * *